(12) United States Patent
Lei et al.

(10) Patent No.: US 9,174,973 B2
(45) Date of Patent: Nov. 3, 2015

(54) CRYSTALLINE FORMS OF AZILSARTAN AND PREPARATION AND USES THEREOF

(71) Applicants: SUNSHINE LAKE PHARMA CO., LTD., Dongguan, Guangdong (CN); RUYUAN HEC PHARM CO., LTD., Ruyuan, Guangdong (CN)

(72) Inventors: Xin Lei, Dongguan (CN); Jinan Peng, Dongguan (CN); Tianming Wang, Dongguan (CN); Zhiqing Lv, Dongguan (CN); Wan Li, Dongguan (CN)

(73) Assignees: SUNSHINE LAKE PHARMA CO., LTD., Dongguan, Guangdong (CN); RUYUAN HEC PHARM CO., LTD., Ruyuan, Guangdong (CN)

( * ) Notice: Subject to any disclaimer, the term of this patent is extended or adjusted under 35 U.S.C. 154(b) by 88 days.

(21) Appl. No.: 14/344,062

(22) PCT Filed: Sep. 27, 2012

(86) PCT No.: PCT/CN2012/082106
§ 371 (c)(1),
(2) Date: Mar. 11, 2014

(87) PCT Pub. No.: WO2013/044816
PCT Pub. Date: Apr. 4, 2013

(65) Prior Publication Data
US 2014/0371279 A1 Dec. 18, 2014

(30) Foreign Application Priority Data

Sep. 30, 2011 (CN) .......................... 2011 1 0304249
Jan. 17, 2012 (CN) .......................... 2012 1 0013952

(51) Int. Cl.
*C07D 413/10* (2006.01)

(52) U.S. Cl.
CPC .................................... *C07D 413/10* (2013.01)

(58) Field of Classification Search
CPC .................................................... C07D 413/10
See application file for complete search history.

(56) References Cited

U.S. PATENT DOCUMENTS

| 5,243,054 A | 9/1993 | Naka et al. |
| 5,354,766 A | 10/1994 | Naka et al. |

(Continued)

FOREIGN PATENT DOCUMENTS

| CN | 102766139 A | 11/2012 |
| CN | 102827153 A | 12/2012 |

(Continued)

OTHER PUBLICATIONS

NIH, Primary Prevention of Hypertension: Clinical and Public Health Advisory from the National High Blood Pressure Education Program, 2002, iv-17.*

(Continued)

*Primary Examiner* — Matthew Coughlin
(74) *Attorney, Agent, or Firm* — Kam. W. Law; Squire Patton Boggs

(57) ABSTRACT

The present invention relates to the field of pharmaceutical chemistry. Disclosed herein is a crystalline form of azilsartan, which is substantially pure. The crystalline form is crystalline form A, form B, form C, form D, form E, form F, form G, form H, form I, form J or form K. The substantially pure crystalline forms of azilsartan of the invention generally have good properties such as high solubility, high bioavailability, good stability, long shelf life and good antistatic property. The crystalline forms of azilsartan generally exhibit an excellent performance in reducing clinical systolic blood pressure (SBP) and average 24-hour SBP. Disclosed herein are methods of preparing the substantially pure crystalline forms of azilsartan, pharmaceutical compositions comprising the crystalline forms, and preparation methods and uses thereof.

19 Claims, 6 Drawing Sheets

(56) References Cited

U.S. PATENT DOCUMENTS

| | | | |
|---|---|---|---|
| 5,583,141 A | 12/1996 | Naka et al. | |
| 6,100,252 A | 8/2000 | Naka et al. | |
| 7,053,192 B2* | 5/2006 | Li et al. | 536/7.4 |
| 2005/0135999 A1* | 6/2005 | Elomari et al. | 423/706 |
| 2007/0032435 A1* | 2/2007 | Alani et al. | 514/18 |
| 2007/0249544 A1* | 10/2007 | Himmelsbach et al. | 514/27 |
| 2008/0004448 A1* | 1/2008 | Wayne et al. | 546/276.7 |
| 2008/0089835 A1* | 4/2008 | Burton | 423/706 |
| 2008/0103186 A1* | 5/2008 | Glover et al. | 514/395 |
| 2008/0139569 A1* | 6/2008 | Rocco et al. | 514/248 |
| 2008/0319024 A1* | 12/2008 | Greil et al. | 514/342 |
| 2009/0069281 A1* | 3/2009 | Austad et al. | 514/183 |
| 2009/0124652 A1* | 5/2009 | Ach et al. | 514/293 |
| 2009/0137794 A1* | 5/2009 | Mendez et al. | 540/78 |
| 2009/0176983 A1* | 7/2009 | Dova et al. | 544/242 |
| 2009/0203705 A1* | 8/2009 | Biagetti et al. | 514/252.02 |
| 2009/0239946 A1* | 9/2009 | McKeown et al. | 514/494 |
| 2010/0021539 A1* | 1/2010 | Kowalski et al. | 424/464 |
| 2012/0238606 A1 | 9/2012 | Lv et al. | |

FOREIGN PATENT DOCUMENTS

| | | |
|---|---|---|
| EP | 520423 A2 * | 12/1992 |
| TW | 251288 | 7/1995 |
| WO | WO 2012139535 A1 * | 10/2012 |
| WO | WO 2012139536 A1 * | 10/2012 |
| WO | WO 2012157977 A2 * | 11/2012 |

OTHER PUBLICATIONS

Baker et al. The Annals of Pharmacotherapy 2001, 45, 1506-1515.*

Kohara et al. J. Med. Chem. 1996, 39, 5228-5235.*

Yasuhisa Kohara et. al., Synthesis and Angiotensin II Receptor Antagonistic Activities of Benzimidazole Bearing Acidic Hererocycles as Novel Tetrazole Bioisosteres, Journal of Medicinal Chemistry (1996), vol. 39, No. 26, pp. 5228-5235.

ISR for PCT/CN2012/082106, dated Jan. 17, 2013.

Written Opinion for PCT/CN2012/082106, dated Jan. 17, 2013.

* cited by examiner

CRYSTALLINE FORMS OF AZILSARTAN AND PREPARATION AND USES THEREOF

CROSS-REFERENCE TO RELATED APPLICATIONS

This is a U.S. national stage application of the International Patent Application No. PCT/CN2012/082106, filed Sep. 27, 2012, which claims priority to Chinese Patent Application No. 201110304249.8, filed Sep. 30, 2011 and Chinese Patent Application No. 201210013952.8, filed Jan. 17, 2012.

TECHNICAL FIELD OF THE INVENTION

The present invention relates to the field of pharmaceutical chemistry. Disclosed herein are novel crystalline forms of azilsartan, pharmaceutical compositions comprising the crystalline forms, and preparation methods and uses thereof.

BACKGROUND OF THE INVENTION

Azilsartan, also known as 1-[[2'-(4,5-Dihydro-5-oxo-1,2,4-oxadiazol-3-yl) [1,1'-biphenyl-4-yl]methyl]-2-ethoxy-1H-benzimidazole-7-carboxylic acid, is a potential angiotensin II receptor antagonist for treating hypertension by oral administration. Azilsartan has formula (I):

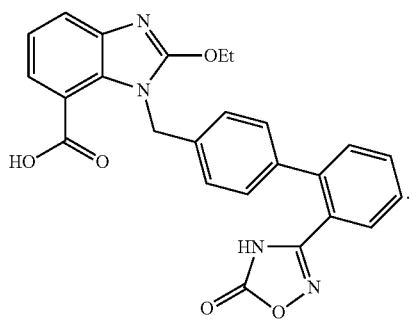

(I)

Azilsartan (TAK-536) is developed by Takeda Pharmaceutical Company Limited (Takeda) in Japan as an angiotensin II receptor antagonist for treating hypertension. Takeda submitted a New Drug Application in Japan on March 2011. Azilsartan can be prepared for administration in the form of a prodrug ester or salt of the prodrug ester such as Azilsartan medoxomil, (5-methyl-2-oxo-1,3-dioxol-4-yl)methyl 2-ethoxy-1-([2'-(5-oxo-4,5-dihydro-1,2,4-oxadiazol-3-yl)biphenyl-4-yl]methyl)-1H-benzimidazole-7-carboxylate, potassium salt, having formula (II):

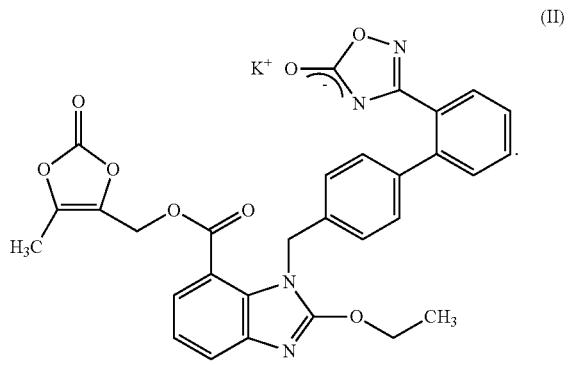 [SMILES: CCOc1nc2cccc(C(=O)OCc3oc(=O)oc3C)c2n1Cc1ccc(-c2ccccc2C2=NO[C-](O)N2)cc1 ; [K+]]

(II)

Azilsartan medoxomil was approved and listed by FDA in February 2011 for once-daily oral treatment of hypertension for adults. Azilsartan medoxomil can be used either alone or in combination with other antihypertensive agents.

Azilsartan is disclosed by Takeda in Chinese patent application CN 93100006.8 (CN 1079966 A). The method of preparation of azilsartan is disclosed in the specification of CN 93100006.8. Example 1 of CN 93100006.8 discloses that azilsartan can be synthesized in four steps. In the final step, the solvent is evaporated completely and then azilsartan is recrystallized from ethyl acetate to obtain colorless prisms of azilsartan with a melting point of 156° C. to 157° C. The synthesis of azilsartan is also disclosed in the J. Med Chem. 1996, 39, pp. 5228-5235 and Chinese Journal of Pharmaceuticals, 2010, 41(12), pp. 881-883. In the final step, azilsartan is recrystallized from anhydrous ethanol to obtain white solid azilsartan with a melting point of 190° C. to 191° C.

However, the above references do not fully characterize the azilsartan polymorphs. Therefore, we do not know the polymorphic forms of the azilsartan polymorphs disclosed in these references. There are many methods that can be used to characterize polymorphs of a drug. Single crystal X-ray diffraction is currently regarded as the most reliable evidence of a particular polymorphic form. However, X-ray powder diffraction can also be used to provide unequivocal proof of polymorphism. Other methods, including microscopy, thermal analysis (e.g., differential scanning calorimetry, thermal gravimetric analysis and hot-stage microscopy), and spectroscopy (e.g., infrared (IR), Raman, solid-state nuclear magnetic resonance (ssNMR)), are also helpful for characterizing polymorphic forms.

A drug such as azilsartan may exist in different crystalline forms, which may have significant differences from each other in appearances, solubilities, melting points, dissolution rates, bioavailabilities, stability, efficacy and the like. However, the currently available crystalline forms of azilsartan have relatively low solubilities, bioavailabilities and/or efficacies.

Therefore, there is a need for novel crystalline forms of azilsartan having better physicochemical properties, especially, relatively higher solubilities, bioavailabilities and/or efficacies. There is also a constant need for a low cost and industrial friendly process for preparing the crystalline forms of azilsartan.

SUMMARY OF THE INVENTION

Provided here is a crystalline form of azilsartan, wherein the crystalline form is form A, form B, form C, form D, form E, form F, form G, form H, form I, form J or form K, and wherein:

a) form A has an X-ray powder diffraction pattern comprising one or more peaks at about 9.15, 18.34, 20.42, 21.49 and 23.53 degrees in term of two theta;

b) form B has an X-ray powder diffraction pattern comprising one or more peaks at about 9.08, 21.41 and 23.47 degrees in term of two theta;

c) form C has an X-ray powder diffraction pattern comprising one or more peaks at about 18.32, 21.85, 23.34 and 24.60 degrees in term of two theta;

d) form D has an X-ray powder diffraction pattern comprising one or more peaks at about 9.33, 9.55, 20.83, 21.82, 25.05 and 26.23 degrees in term of two theta;

e) form E has an X-ray powder diffraction pattern comprising one or more peaks at about 9.20, 10.42, 18.04, 21.53, 23.05, 23.57 and 23.89 degrees in term of two theta;

f) form F has an X-ray powder diffraction pattern comprising one or more peaks at about 9.09, 9.22 and 18.29 degrees in term of two theta;

g) form G has an X-ray powder diffraction pattern comprising one or more peaks at about 9.18 and 18.37 degrees in term of two theta;

h) form H has an X-ray powder diffraction pattern comprising one or more peaks at about 7.52, 21.09, 22.05 and 23.21 degrees in term of two theta;

i) form I has an X-ray powder diffraction pattern comprising one or more peaks at about 7.41, 8.57, 18.27 and 21.01 degrees in term of two theta;

j) form J has an X-ray powder diffraction pattern comprising one or more peaks at about 21.30, 22.81 and 23.32 degrees in term of two theta; or k) form K has an X-ray powder diffraction pattern comprising one or more peaks at about 7.58, 8.52, 17.03, 21.16, 21.56, 22.14 and 22.88 degrees in term of two theta.

Figure 1:
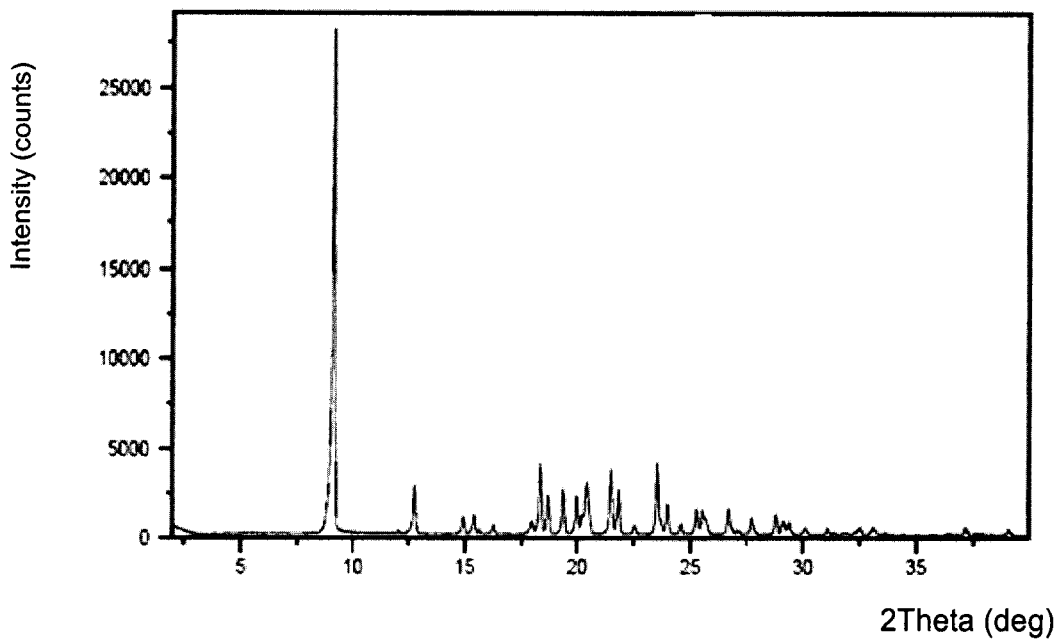
FIG. 1 depicts the X-ray powder diffractogram of the crystalline form A of azilsartan.

In some embodiments, form A has an X-ray powder diffraction pattern comprising one or more peaks at about 9.15, 12.75, 18.34, 18.68, 19.36, 19.97, 20.42, 21.49, 21.82, 23.53, 23.98 and 25.26 degrees in term of two theta; or an X-ray powder diffraction pattern comprising one or more peaks at about 9.15, 12.75, 14.91, 15.38, 17.98, 18.34, 18.68, 19.36, 19.97, 20.42, 21.49, 21.82, 23.53, 23.98, 24.60, 25.26, 25.53, 26.68, 27.72, 28.77, 29.11 and 29.40 degrees in term of two theta; or an X-ray powder diffraction pattern substantially as depicted in FIG. 1 wherein the peak at about 9.15 degree in term of two theta has a relative intensity of at least about 50%, at least about 60%, at least about 70%, at least about 80%, at least about 90% or at least about 99% with respect to the strongest peak in the X-ray powder diffraction pattern.

Figure 2:
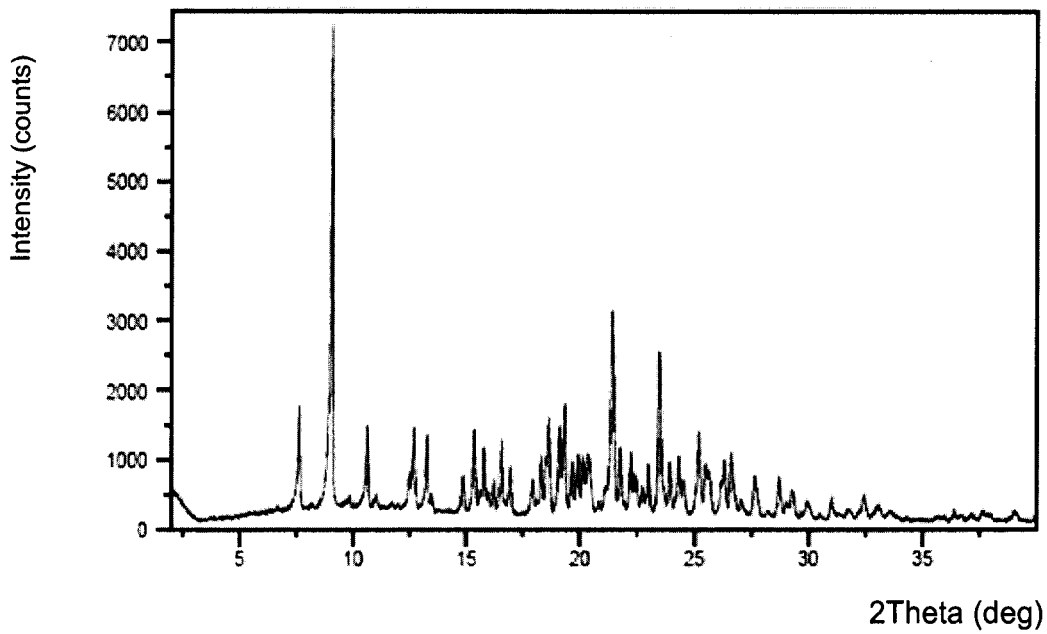
FIG. 2 depicts the X-ray powder diffractogram of the crystalline form B of azilsartan.

In some embodiments, form B has an X-ray powder diffraction pattern comprising one or more peaks at about 7.63, 9.08, 18.62, 19.30, 21.41 and 23.47 degrees in term of two theta; or an X-ray powder diffraction pattern comprising one or more peaks at about 7.63, 9.08, 10.62, 12.69, 13.24, 15.34, 15.75, 16.53, 16.95, 18.27, 18.62, 19.08, 19.30, 19.64, 19.89, 20.10, 20.35, 21.41, 21.76, 22.21, 22.98, 23.47, 23.92, 24.31, 25.18, 25.48, 26.31 and 26.62 degrees in term of two theta; or an X-ray powder diffraction pattern substantially as depicted in FIG. 2 wherein the peak at about 9.08 degree in term of two theta has a relative intensity of at least about 50%, at least about 60%, at least about 70%, at least about 80%, at least about 90% or at least about 99% with respect to the strongest peak in the X-ray powder diffraction pattern.

Figure 3:
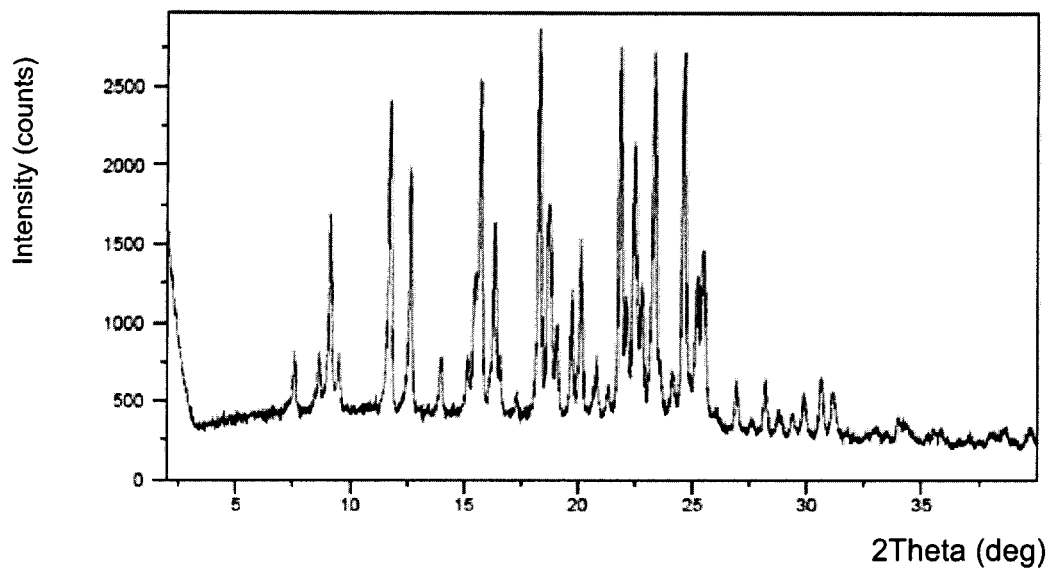
FIG. 3 depicts the X-ray powder diffractogram of the crystalline form C of azilsartan.

In some embodiments, form C has an X-ray powder diffraction pattern comprising one or more peaks at about 9.13, 11.77, 15.74, 16.33, 18.32, 18.68, 21.85, 22.46, 23.34 and 24.60 degrees in term of two theta; or an X-ray powder diffraction pattern comprising one or more peaks at about 7.56, 9.13, 11.77, 13.97, 15.74, 16.33, 18.32, 18.68, 19.07, 19.72, 20.12, 20.77, 21.85, 22.12, 22.46, 22.83, 23.34, 24.12, 24.60, 25.20, 25.51, 26.91, 28.17, 29.87, 30.60 and 31.09 degrees in term of two theta; or an X-ray powder diffraction pattern substantially as depicted in FIG. 3 wherein the peak at about 18.32 degree in term of two theta has a relative intensity of at least about 50%, at least about 60%, at least about 70%, at least about 80%, at least about 90% or at least about 99% with respect to the strongest peak in the X-ray powder diffraction pattern.

Figure 4:
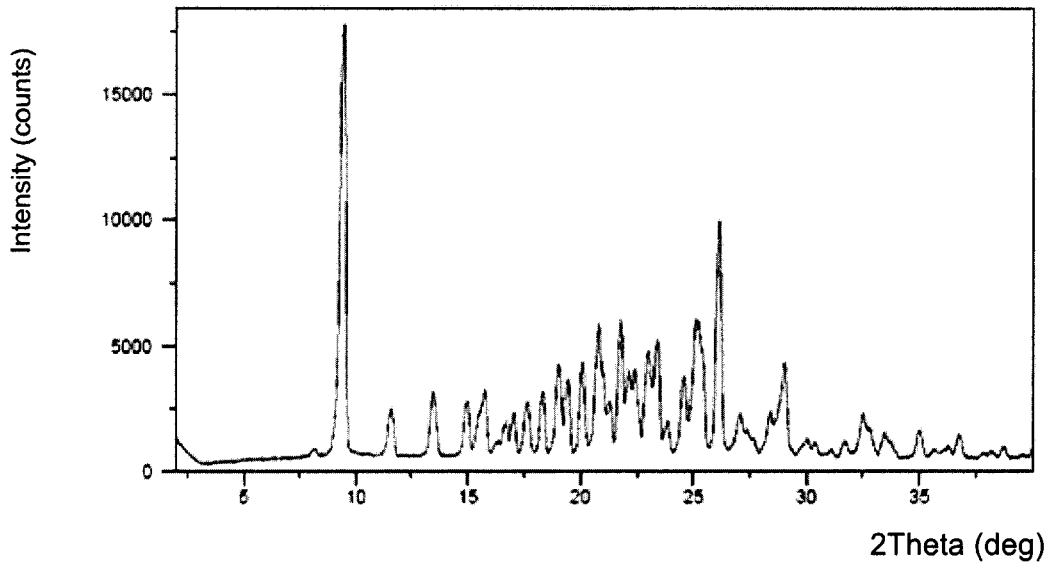
FIG. 4 depicts the X-ray powder diffractogram of the crystalline form D of azilsartan.

In some embodiments, form D has an X-ray powder diffraction pattern comprising one or more peaks at about 9.33, 9.55, 11.65, 13.46, 14.99, 15.83, 17.69, 18.39, 19.11, 19.51, 20.16, 20.83, 21.36, 21.67, 21.82, 22.15, 22.38, 23.02, 23.48, 24.63, 25.05, 25.46, 25.99, 26.23, 27.09, 28.40, 29.09 and 32.49 degrees in term of two theta; or an X-ray powder diffraction pattern substantially as depicted in FIG. 4 wherein the peak at about 9.33 degree in term of two theta has a relative intensity of at least about 50%, at least about 60%, at least about 70%, at least about 80%, at least about 90% or at least about 99% with respect to the strongest peak in the X-ray powder diffraction pattern.

Figure 5:
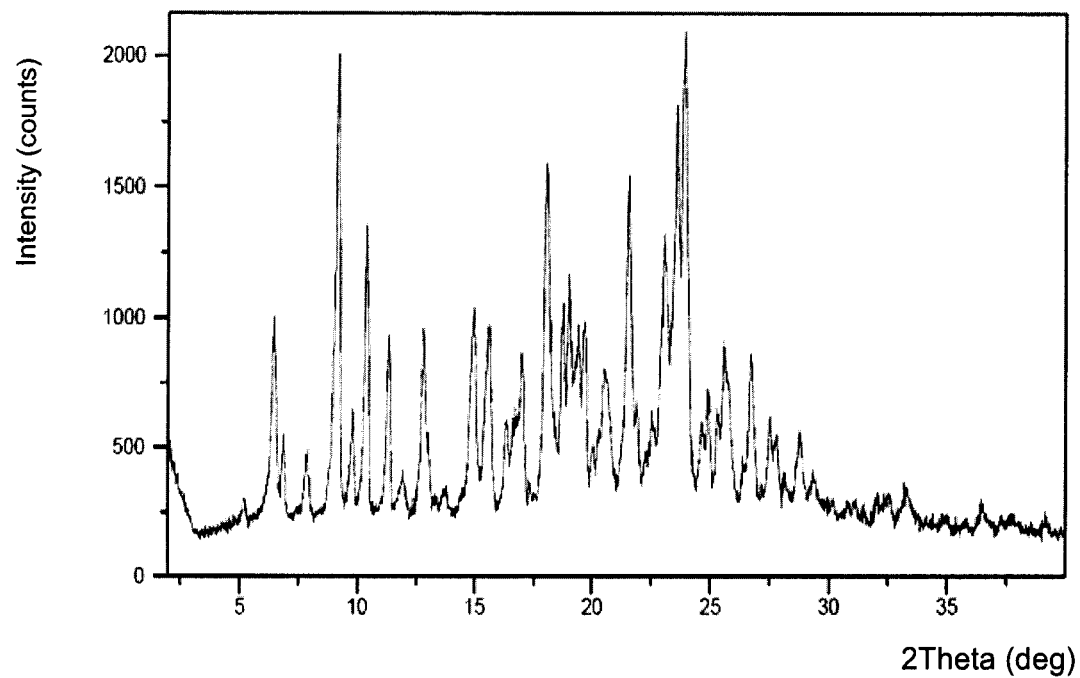
FIG. 5 depicts the X-ray powder diffractogram of the crystalline form E of azilsartan.

In some embodiments, form E has an X-ray powder diffraction pattern comprising one or more peaks at about 6.48, 9.20, 10.42, 11.36, 12.81, 14.97, 15.62, 16.32, 17.03, 18.04, 18.72, 19.00, 19.67, 20.55, 21.53, 23.05, 23.57, 23.89, 24.91, 25.65 and 26.70 degrees in term of two theta; or an X-ray powder diffraction pattern comprising one or more peaks at about 6.48, 6.87, 7.87, 9.20, 9.81, 10.42, 11.36, 11.94, 12.81, 14.97, 15.62, 16.32, 17.03, 18.04, 18.72, 19.00, 19.67, 20.55, 21.53, 23.05, 23.57, 23.89, 24.91, 25.65, 26.70, 27.61 and 28.80 degrees in term of two theta; or an X-ray powder diffraction pattern substantially as depicted in FIG. 5 wherein the peak at about 23.89 degree in term of two theta has a relative intensity of at least about 50%, at least about 60%, at least about 70%, at least about 80%, at least about 90% or at least about 99% with respect to the strongest peak in the X-ray powder diffraction pattern.

Figure 6:
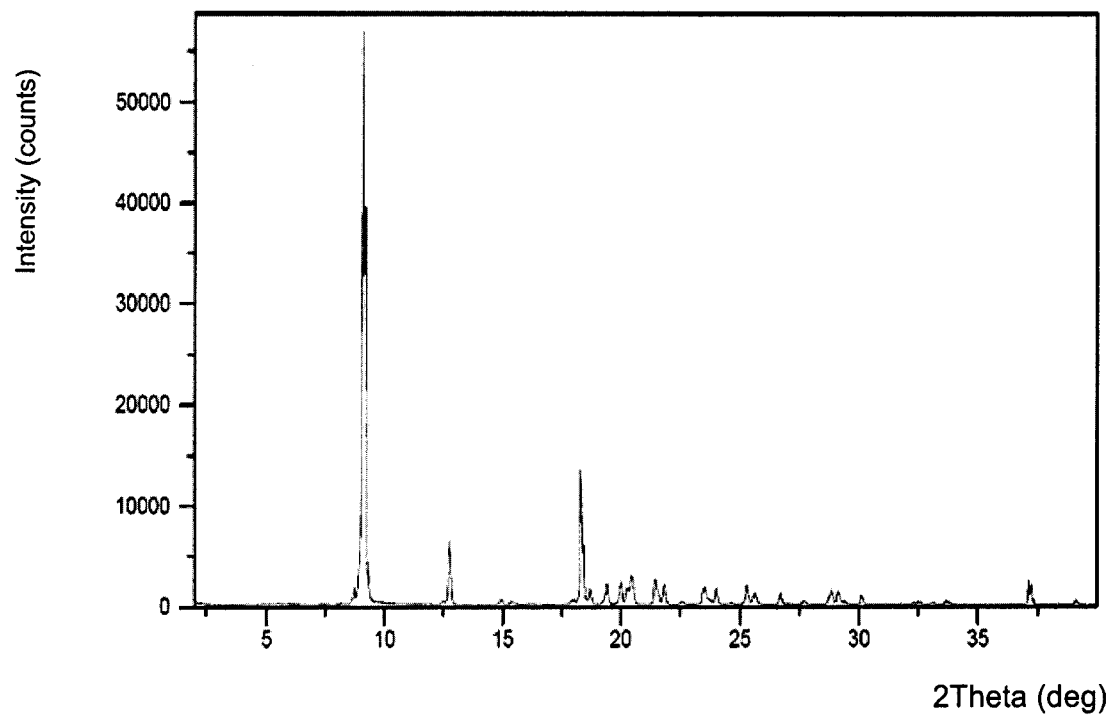
FIG. 6 depicts the X-ray powder diffractogram of the crystalline form F of azilsartan.

In some embodiments, form F has an X-ray powder diffraction pattern comprising one or more peaks at about 9.09, 9.22, 12.76, 18.29, 18.44, 18.71, 19.41, 20.01, 20.24, 20.44, 21.45, 21.82, 23.44, 23.54, 24.01, 25.30, 25.65, 26.72, 28.86, 29.10, 37.14 and 37.26 degrees in term of two theta; or an X-ray powder diffraction pattern substantially as depicted in FIG. 6 wherein the peak at about 9.09 degree in term of two theta has a relative intensity of at least about 50%, at least about 60%, at least about 70%, at least about 80%, at least about 90% or at least about 99% with respect to the strongest peak in the X-ray powder diffraction pattern.

Figure 7:
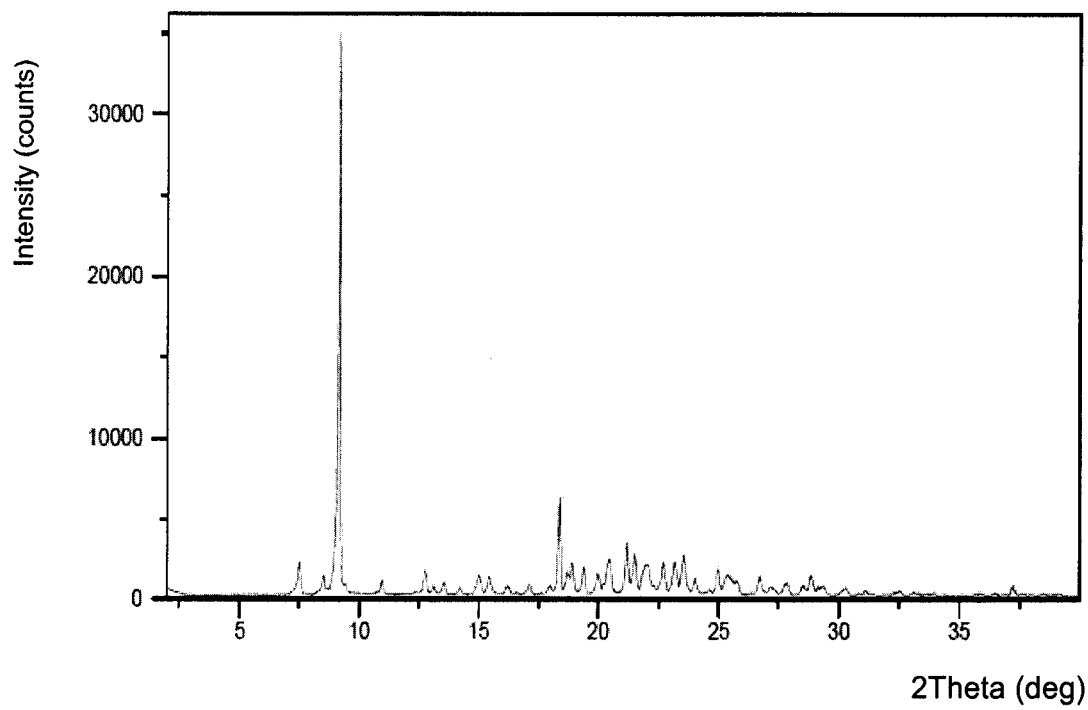
FIG. 7 depicts the X-ray powder diffractogram of the crystalline form G of azilsartan.

In some embodiments, form G has an X-ray powder diffraction pattern comprising one or more peaks at about 7.51, 8.52, 9.18, 10.96, 12.74, 13.12, 13.56, 14.22, 15.03, 15.43, 16.22, 17.10, 17.96, 18.37, 18.71, 19.38, 19.97, 20.47, 21.16, 21.53, 21.85, 22.07, 22.71, 23.17, 23.54, 24.02, 24.96, 25.36, 25.78 and 26.72 degrees in term of two theta; or an X-ray powder diffraction pattern substantially as depicted in FIG. 7 wherein the peak at about 9.18 degree in term of two theta has a relative intensity of at least about 50%, at least about 60%, at least about 70%, at least about 80%, at least about 90% or at least about 99% with respect to the strongest peak in the X-ray powder diffraction pattern.

Figure 8:
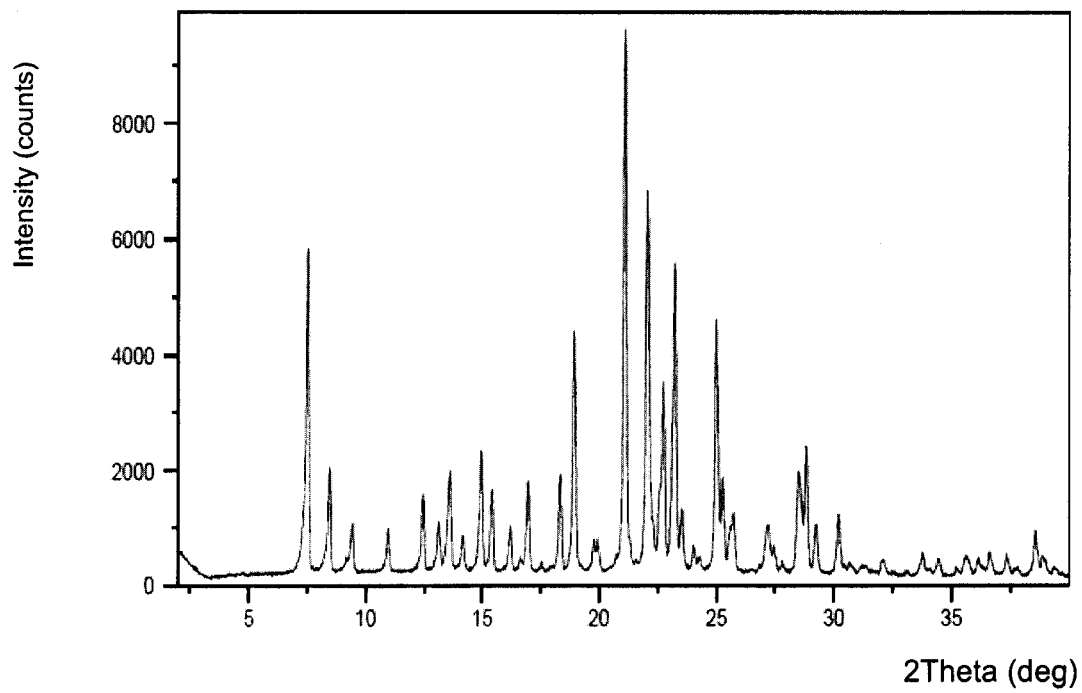
FIG. 8 depicts the X-ray powder diffractogram of the crystalline form H of azilsartan.

In some embodiments, form H has an X-ray powder diffraction pattern comprising one or more peaks at about 7.52, 8.45, 14.93, 18.92, 19.94, 21.09, 22.05, 22.71, 23.21, 24.98 and 28.80 degrees in term of two theta; or an X-ray powder diffraction pattern comprising one or more peaks at about 7.52, 8.45, 9.44, 10.97, 12.45, 13.14, 13.61, 14.15, 14.93, 15.40, 16.18, 16.95, 18.32, 18.92, 19.94, 21.09, 22.05, 22.71, 23.21, 23.52, 24.98, 25.26, 25.71, 27.22, 28.47, 28.80, 29.22 and 30.15 degrees in term of two theta; or an X-ray powder diffraction pattern substantially as depicted in FIG. 8 wherein the peak at about 21.09 degree in term of two theta has a relative intensity of at least about 50%, at least about 60%, at least about 70%, at least about 80%, at least about 90% or at least about 99% with respect to the strongest peak in the X-ray powder diffraction pattern.

Figure 9:
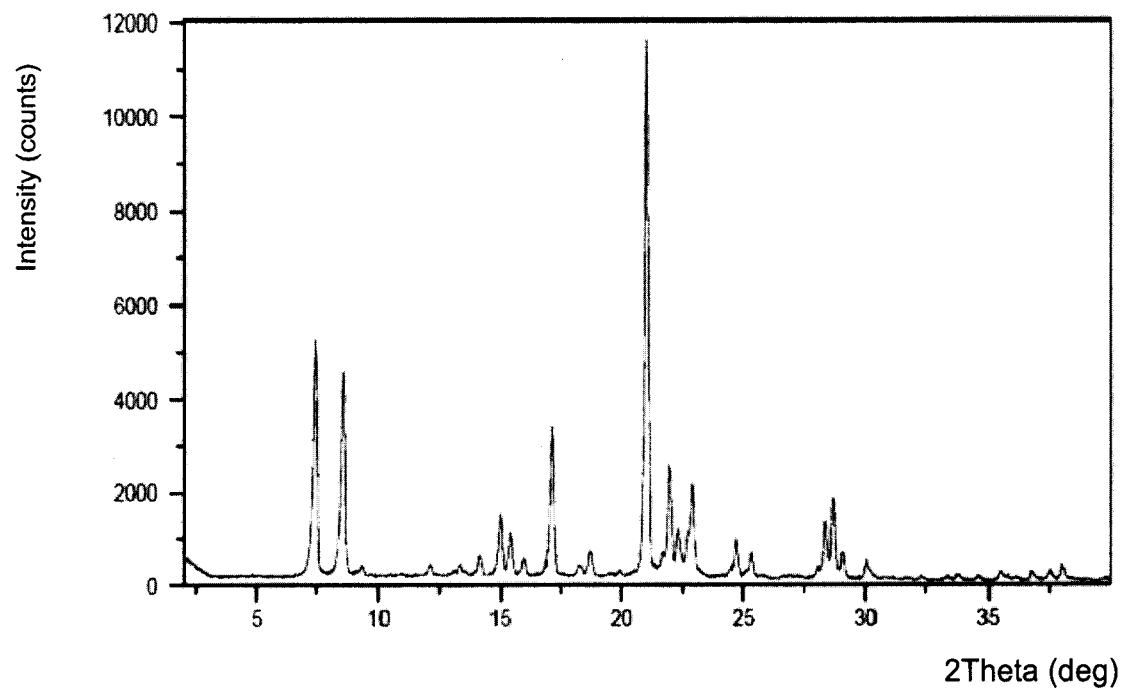
FIG. 9 depicts the X-ray powder diffractogram of the crystalline form I of azilsartan.

In some embodiments, form I has an X-ray powder diffraction pattern comprising one or more peaks at about 7.41, 8.57, 12.13, 14.18, 15.02, 15.39, 15.98, 17.08, 18.27, 18.73, 21.01, 21.92, 22.31, 22.91, 24.66, 25.36, 28.27, 28.61 and 29.07 degrees in term of two theta; or an X-ray powder diffraction pattern substantially as depicted in FIG. 9 wherein the peak at about 21.01 degree in term of two theta has a relative intensity of at least about 50%, at least about 60%, at least about 70%, at least about 80%, at least about 90% or at least about 99% with respect to the strongest peak in the X-ray powder diffraction pattern.

Figure 10:
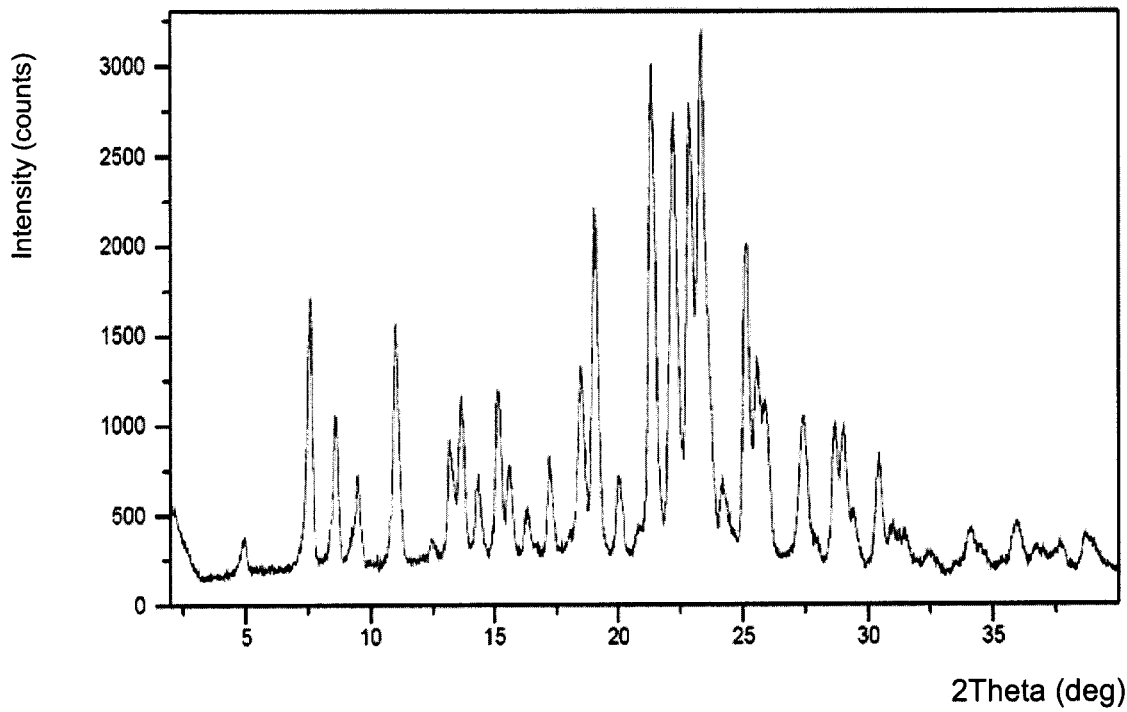
FIG. 10 depicts the X-ray powder diffractogram of the crystalline form J of azilsartan.

In some embodiments, form J has an X-ray powder diffraction pattern comprising one or more peaks at about 7.61, 19.00, 21.30, 22.10, 22.81, 23.32 and 25.05 degrees in term of two theta; or an X-ray powder diffraction pattern comprising one or more peaks at about 2.10, 4.93, 7.61, 8.64, 9.50, 10.99, 13.17, 13.64, 14.30, 15.12, 15.57, 16.25, 17.21, 18.49, 19.00, 19.99, 21.30, 22.10, 22.81, 23.32, 24.19, 25.05, 25.55, 25.96, 27.43, 28.64, 29.04 and 30.43 degrees in term of two theta; or an X-ray powder diffraction pattern substantially as depicted in FIG. 10 wherein the peak at about 23.32 degree in term of two theta has a relative intensity of at least about 50%, at least about 60%, at least about 70%, at least about 80%, at least about 90% or at least about 99% with respect to the strongest peak in the X-ray powder diffraction pattern.

Figure 11:
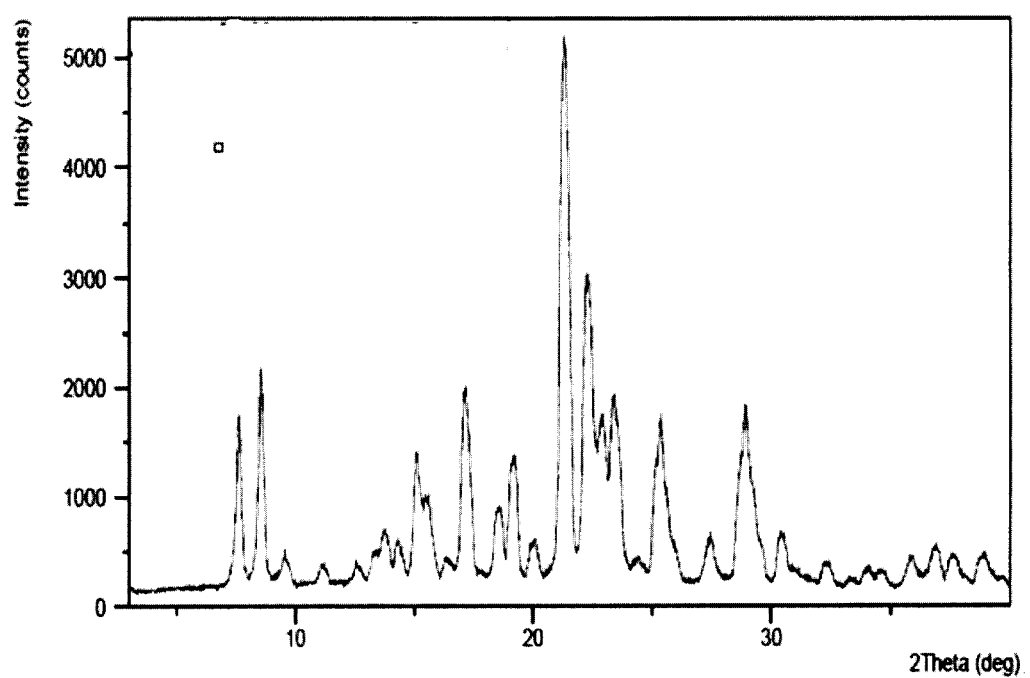
FIG. 11 depicts the X-ray powder diffractogram of the crystalline form K of azilsartan.

In some embodiments, form K has an X-ray powder diffraction pattern comprising one or more peaks at about 7.58, 8.52, 13.77, 15.05, 15.56, 17.03, 18.67, 19.03, 19.27, 20.04, 21.16, 21.56, 22.14, 22.88, 23.31, 23.66, 25.08, 25.36, 27.48, 28.65 and 28.90 degrees in term of two theta; or an X-ray powder diffraction pattern substantially as depicted in FIG. 11 wherein the peak at about 21.16 degree in term of two theta has a relative intensity of at least about 50%, at least about 60%, at least about 70%, at least about 80%, at least about 90% or at least about 99% with respect to the strongest peak in the X-ray powder diffraction pattern.

Also provided herein is a process for preparing the crystalline forms A-K of azilsartan, comprising dissolving azilsartan in a good solvent to form a solution; and forming crystals by cooling the solution.

Also provided herein is a pharmaceutical composition comprising the crystalline forms A-K of azilsartan and one or more of inert excipients or carriers.

Also provided herein is a method of preventing or treating hypertension in a patient by administering to the patient a pharmaceutically effective amount of the crystalline forms A-K of azilsartan.

DESCRIPTION OF THE INVENTION

Definitions and General Terminology

As used herein, the term "crystalline form" of a compound refers to a unique ordered arrangement and/or conformations of molecules in the crystal lattice of the compound.

As used herein, a crystalline form that is "substantially pure" refers to a crystalline form that is substantially free of one or more other crystalline forms, i.e., the crystalline form has a purity of at least about 60%, at least about 70%, at least about 80%, at least about 85%, at least about 90%, at least about 93%, at least about 95%, at least about 98%, at least about 99%, at least about 99.5%, at least about 99.6%, at least about 99.7%, at least about 99.8%, or at least about 99.9%; or the crystalline form has less than 20%, less than 10%, less than 5%, less than 3%, less than 1%, less than 0.5%, less than 0.1%, or less than 0.01% of the one or more other crystalline forms, based on the total volume or weight of the crystalline form and the one or more other crystalline form.

As used herein, a crystalline form that is "substantially free" of one or more other crystalline forms refers to a crystalline form containing less than 20%, less than 10%, less than 5%, less than 4%, less than 3%, less than 2%, less than 1%, less than 0.5%, less than 0.1%, or less than 0.01% of the one or more other crystalline form, based on the total volume or weight of the crystalline form and the one or more other crystalline form.

As used herein, an X-ray powder diffraction pattern that is "substantially as depicted" in a figure refers to an X-ray powder diffraction pattern having at least 50%, at least 60%, at least 70%, at least 80%, at least 90%, at least 95%, or at least 99% of the peaks shown in the figure.

As used herein, the term "relative intensity" refers to the intensity of a peak with respect to the intensity of the strongest peak in the X-ray powder diffraction (XRPD) pattern which is regarded as 100%.

As used herein, the term "good solvent" refers to a solvent in which azilsartan has a solubility greater than 1 g/L, greater than 2 g/L, greater than 3 g/L, greater than 4 g/L, greater than 5 g/L, greater than 6 g/L, greater than 7 g/L, greater than 8 g/L, greater than 9 g/L, greater than 10 g/L, greater than 15 g/L, greater than 20 g/L, greater than 30 g/L, greater than 40 g/L, greater than 50 g/L, greater than 60 g/L, greater than 70 g/L, greater than 80 g/L, or greater than 100 g/L of the solvent. In some embodiments, the solubility of azilsartan in the good solvent is greater than the solubility of azilsartan in the anti-solvent. In certain embodiments, the solubility difference between the good solvent and anti-solvent is about 10%, 20%, 30%, 40%, 50%, 60%, 70%, 80% or 90%, based on the solubility of the good solvent. In some embodiments, the solubility of the good solvent is about 10%, 20%, 30%, 40%, 50%, 60%, 70%, 80% or 90% higher than anti-solvent.

As used herein, the term "anti-solvent" refers to a solvent which can promote supersaturation and/or crystallization. In some embodiments, the solubility of azilsartan in the anti-solvent is less than 0.001 g/L, less than 0.01 g/L, less than 0.1 g/L, less than 0.2 g/L, less than 0.3 g/L, less than 0.4 g/L, less than 0.5 g/L, less than 0.6 g/L, less than 0.8 g/L, less than 1 g/L, less than 2 g/L, less than 3 g/L, less than 4 g/L, less than 5 g/L, less than 6 g/L, less than 7 g/L, less than 8 g/L, less than 9 g/L, or less than 10 g/L of the anti-solvent.

As used herein, the term "room temperature" refers to a temperature from about 18° C. to about 30° C. or a temperature from about 20° C. to about 24° C. or a temperature at about 22° C.

As used herein, the term "overnight" refers to a period of from about 13 hours to about 24 hours, or from about 16 hours to about 24 hours.

As used herein, when referring to a spectrum and/or to data presented in a graph, the term "peak" refers to a feature that one skilled in the art would recognize as not attributable to background noise.

In the following description, all numbers disclosed herein are approximate values, regardless whether the word "about" or "approximate" is used in connection therewith. The value of each number may differ by 1%, 2%, 5%, 7%, 8%, 10%, 15% or 20%. Therefore, whenever a number having a value N is disclosed, any number having the value N+/−1%, N+/−2%, N+/−3%, N+/−5%, N+/−7%, N+/−8%, N+/−10%, N+/−15% or N+/−20% is specifically disclosed, wherein "+/−" refers to plus or minus. Whenever a numerical range with a lower limit, $R^L$, and an upper limit, $R^U$, is disclosed, any number falling within the range is specifically disclosed. In particular, the following numbers within the range are specifically disclosed: $R=R^L+k*(R^U-R^L)$, wherein k is a variable ranging from 1% to 100% with a 1% increment, i.e., k is 1%, 2%, 3%, 4%, 5%, . . . , 50%, 51%, 52%, . . . , 95%, 96%, 97%, 98%, 99%, or 100%. Moreover, any numerical range defined by two R numbers as defined above is also specifically disclosed.

The present invention provides a novel crystalline form of azilsartan and its preparation thereof.

Provided herein are novel crystalline forms of azilsartan. The crystalline forms of a drug compound may have different chemical and physical properties, including melting point, chemical reactivity, apparent solubility, dissolution rate, optical and mechanical properties, vapor pressure and density. These properties can have a direct effect on the ability to process and/or manufacture the drug compound and the drug product, as well as on drug product stability, dissolution, and bioavailability. Thus the crystalline forms of azilsartan can affect the quality, safety, and efficacy of a drug product comprising azilsartan.

The principal embodiment of the present invention is to investigate whether azilsartan can exist in crystalline form. Unexpectedly, we have found that Azilsartan can exist in many novel crystalline forms including form A, form B, form C, form D, form E, form F, form G, form H, form I, form J and form K. In some embodiments, each of the novel crystalline form of azilsartan is substantially pure.

The crystalline forms of azilsartan may exhibit increased solubility and thermal stability; may provide better oral bioavailability and/or a better dissolution profile for a particular formulation; may also provide free-flowing easily filterable, and/or thermally stable characteristics that are suitable for use in particular formulations. The – crystalline forms of azilsartan have low electrostatic property which is convenient to the operation of the production process. The – crystalline forms of azilsartan may exhibit reducing clinical systolic blood pressure (SBP) and have a good performance in term of the 24-hour average clinical systolic. Therefore, they are suitable for preparing pharmaceutical compositions for the prevention and/or treatment of hypertension.

In some embodiments, the crystalline form of azilsartan is crystalline form A. In certain embodiments, form A of azilsartan disclosed herein is substantially pure. In some embodiments, form A has an X-ray powder diffraction pattern (XRPD) comprising a peak at about 9.15 degree in term of two theta. In certain embodiments, form A has an XRPD comprising one or more peaks at about 9.15, 18.34, 20.42, 21.49 and 23.53 degrees in term of two theta. In some embodiments, form A has an XRPD comprising one or more peaks at about 9.15, 12.75, 18.34, 18.68, 19.36, 19.97, 20.42, 21.49, 21.82, 23.53, 23.98 and 25.26 degrees in term of two theta. In some embodiments, form A has an XRPD comprising one or more peaks at about 9.15, 12.75, 14.91, 15.38, 17.98, 18.34, 18.68, 19.36, 19.97, 20.42, 21.49, 21.82, 23.53, 23.98, 24.60, 25.26, 25.53, 26.68, 27.72, 28.77, 29.11 and 29.40 degrees in term of two theta. In some embodiments, form A has an XRPD substantially as depicted in FIG. 1 wherein the peak at about 9.15 degree in term of two theta has a relative intensity of at least about 50%, at least about 60%, at least about 70%, at least about 80%, at least about 90%, at least about 99% with respect to the strongest peak in the XRPD.

In certain embodiments, the characteristics of form A can be detected, identified, classified and characterized using well-known techniques such as, but not limited to, melting point. The melting point of form A is at about 200.2° C. to about 213.7° C.

In some embodiments, the crystalline form of azilsartan is crystalline form B. In some embodiments, form B of azilsartan disclosed herein is substantially pure. In some embodiments, form B has an XRPD comprising a peak at about 9.08 degree in term of two theta. In some embodiments, form B has an XRPD comprising one or more peaks at about 9.08, 21.41 and 23.47 degrees in term of two theta; or an XRPD comprising one or more peaks at about 7.63, 9.08, 18.62, 19.30, 21.41 and 23.47 degrees in term of two theta. In some embodiments, form B has an XRPD comprising one or more peaks at about 7.63, 9.08, 10.62, 12.69, 13.24, 15.34, 15.75, 16.53, 16.95, 18.27, 18.62, 19.08, 19.30, 19.64, 19.89, 20.10, 20.35, 21.41, 21.76, 22.21, 22.98, 23.47, 23.92, 24.31, 25.18, 25.48, 26.31 and 26.62 degrees in term of two theta. In some embodiments, form B has an XRPD substantially as depicted in FIG. 2 wherein the peak at about 9.08 degree in term of two theta has a relative intensity of at least about 50%, at least about 60%, at least about 70%, at least about 80%, at least about 90% or at least about 99% with respect to the strongest peak in the XRPD.

In certain embodiments, the characteristics of form B can be detected, identified, classified and characterized using well-known techniques such as, but not limited to, melting point. The melting point of form B is at about 196.9° C. to about 198.6° C.

In some embodiments, the crystalline form of azilsartan is crystalline form C. In some embodiments, form C of azilsartan disclosed herein is substantially pure. In some embodiments, form C has an XRPD comprising a peak at about 18.32 degree in term of two theta. In some embodiments, form C has an XRPD comprising one or more peaks at about 18.32, 21.85, 23.34 and 24.60 degrees in term of two theta. In some embodiments, form C has an XRPD comprising one or more peaks at about 9.13, 11.77, 15.74, 16.33, 18.32, 18.68, 21.85, 22.46, 23.34 and 24.60 degrees in term of two theta. In some embodiments, form C has an XRPD comprising one or more peaks at about 7.56, 9.13, 11.77, 13.97, 15.74, 16.33, 18.32, 18.68, 19.07, 19.72, 20.12, 20.77, 21.85, 22.12, 22.46, 22.83, 23.34, 24.12, 24.60, 25.20, 25.51, 26.91, 28.17, 29.87, 30.60 and 31.09 degrees in term of two theta. In some embodiments, form C has an XRPD substantially as depicted in FIG. 3 wherein the peak at about 18.32 degree in term of two theta has a relative intensity of at least about 50%, at least about 60%, at least about 70%, at least about 80%, at least about 90% or at least about 99% with respect to the strongest peak in the XRPD.

In certain embodiments, the characteristics of form C can be detected, identified, classified and characterized using well-known techniques such as, but not limited to, melting point. The melting point of form C is at about 202.2° C. to about 204.1° C.

In some embodiments, the crystalline form of azilsartan is crystalline form D. In some embodiments, form D of azilsartan disclosed herein is substantially pure. In some embodiments, form D has an XRPD comprising a peak at about 9.33 degree in term of two theta. In some embodiments, form D has an XRPD comprising one or more peaks at about 9.33, 9.55, 20.83, 21.82, 25.05 and 26.23 degrees in term of two theta. In some embodiments, form D has an XRPD comprising one or more peaks at about 9.33, 9.55, 11.65, 13.46, 14.99, 15.83, 17.69, 18.39, 19.11, 19.51, 20.16, 20.83, 21.36, 21.67, 21.82, 22.15, 22.38, 23.02, 23.48, 24.63, 25.05, 25.46, 25.99, 26.23, 27.09, 28.40, 29.09 and 32.49 degrees in term of two theta. In some embodiments, form D has an XRPD substantially as depicted in FIG. 4 wherein the peak at about 9.33 degree in term of two theta has a relative intensity of at least about 50%, at least about 60%, at least about 70%, at least about 80%, at least about 90% or at least about 99% with respect to the strongest peak in the XRPD.

In certain embodiments, the characteristics of form D can be detected, identified, classified and characterized using well-known techniques such as, but not limited to, melting point. The melting point of form D is at about 171.6° C. to about 176.2° C.

In some embodiments, the crystalline form of azilsartan is crystalline form E. In some embodiments, form E of azilsartan disclosed herein is substantially pure. In some embodiments, form E has an XRPD comprising a peak at about 23.89 degree in term of two theta. In some embodiments, form E has an XRPD comprising one or more peaks at about 9.20, 10.42, 18.04, 21.53, 23.05, 23.57 and 23.89 degrees in term of two theta. In some embodiments, form E has an XRPD comprising one or more peaks at about 6.48, 9.20, 10.42, 11.36, 12.81, 14.97, 15.62, 16.32, 17.03, 18.04, 18.72, 19.00, 19.67, 20.55, 21.53, 23.05, 23.57, 23.89, 24.91, 25.65 and 26.70 degrees in term of two theta. In some embodiments, form E has an XRPD comprising one or more peaks at about 6.48, 6.87, 7.87, 9.20, 9.81, 10.42, 11.36, 11.94, 12.81, 14.97, 15.62, 16.32, 17.03, 18.04, 18.72, 19.00, 19.67, 20.55, 21.53, 23.05, 23.57, 23.89, 24.91, 25.65, 26.70, 27.61 and 28.80 degrees in term of two theta. In some embodiments, form E has an XRPD substantially as depicted in FIG. 5 wherein the peak at about 23.89 degree in term of two theta has a relative intensity of at least about 50%, at least about 60%, at least about 70%, at least about 80%, at least about 90% or at least about 99% with respect to the strongest peak in the XRPD.

In certain embodiments, the characteristics of form E can be detected, identified, classified and characterized using well-known techniques such as, but not limited to, melting point. The melting point of form E is at about 197.5° C. to about 201.3° C.

In some embodiments, the crystalline form of azilsartan is crystalline form F. In some embodiments, form F of azilsartan disclosed herein is substantially pure.—In some embodiments, form F has an XRPD comprising a peak at about 9.09 degree in term of two theta. In some embodiments, form F has an XRPD comprising one or more peaks at about 9.09, 9.22 and 18.29 degrees in term of two theta. In some embodiments, form F has an XRPD comprising one or more peaks at about 9.09, 9.22, 12.76, 18.29, 18.44, 18.71, 19.41, 20.01, 20.24, 20.44, 21.45, 21.82, 23.44, 23.54, 24.01, 25.30, 25.65, 26.72, 28.86, 29.10, 37.14 and 37.26 degrees in term of two theta. In some embodiments, form F has an XRPD substantially as depicted in FIG. 6 wherein the peak at about 9.09 degree in term of two theta has a relative intensity of at least about 50%, at least about 60%, at least about 70%, at least about 80%, at least about 90% or at least about 99% with respect to the strongest peak in the XRPD.

In certain embodiments, the characteristics of form F can be detected, identified, classified and characterized using well-known techniques such as, but not limited to, melting point. The melting point of form F is at about 201.6° C. to about 204.6° C.

In some embodiments, the crystalline form of azilsartan is crystalline form G. In some embodiments, form G of azilsartan disclosed herein is substantially pure. In some embodiments, form G has an XRPD comprising a peak at about 9.18 degree in term of two theta. In some embodiments, form G has an XRPD comprising one or more peaks at about 9.18 and 18.37 degrees in term of two theta. In some embodiments, form G has an XRPD comprising one or more peaks at about 7.51, 8.52, 9.18, 10.96, 12.74, 13.12, 13.56, 14.22, 15.03, 15.43, 16.22, 17.10, 17.96, 18.37, 18.71, 19.38, 19.97, 20.47, 21.16, 21.53, 21.85, 22.07, 22.71, 23.17, 23.54, 24.02, 24.96, 25.36, 25.78 and 26.72 degrees in term of two theta. In some embodiments, form G has an XRPD substantially as depicted in FIG. 7 wherein the peak at about 9.18 degree in term of two theta has a relative intensity of at least about 50%, at least about 60%, at least about 70%, at least about 80%, at least about 90% or at least about 99% with respect to the strongest peak in the XRPD.

In certain embodiments, the characteristics of form G can be detected, identified, classified and characterized using well-known techniques such as, but not limited to, melting point. The melting point of form G is at about 203.5° C. to about 205.1° C.

In some embodiments, the crystalline form of azilsartan is crystalline form H. In some embodiments, form H of azilsartan disclosed herein is substantially pure.—In some embodiments, form H has an XRPD comprising a peak at about 21.09 degree in term of two theta. In some embodiments, form H has an XRPD comprising one or more peaks at about 7.52, 21.09, 22.05 and 23.21 degrees in term of two theta. In some embodiments, form H has an XRPD comprising one or more peaks at about 7.52, 8.45, 14.93, 18.92, 19.94, 21.09, 22.05, 22.71, 23.21, 24.98 and 28.80 degrees in term of two theta. In some embodiments, form H has an XRPD comprising one or more peaks at about 7.52, 8.45, 9.44, 10.97, 12.45, 13.14, 13.61, 14.15, 14.93, 15.40, 16.18, 16.95, 18.32, 18.92, 19.94, 21.09, 22.05, 22.71, 23.21, 23.52, 24.98, 25.26, 25.71, 27.22, 28.47, 28.80, 29.22 and 30.15 degrees in term of two theta. In some embodiments, form H has an XRPD substantially as depicted in FIG. 8 wherein the peak at about 21.09 degree in term of two theta has a relative intensity of at least about 50%, at least about 60%, at least about 70%, at least about 80%, at least about 90% or at least about 99% with respect to the strongest peak in the XRPD.

In certain embodiments, the characteristics of form H can be detected, identified, classified and characterized using well-known techniques such as, but not limited to, melting point. The melting point of form H is at about 190.8° C. to about 192.0° C.

In some embodiments, the crystalline form of azilsartan is crystalline form I. In some embodiments, form I of azilsartan disclosed herein is substantially pure. In some embodiments, form I has an XRPD comprising a peak at about 21.01 degree in term of two theta. In some embodiments, form I has an XRPD comprising one or more peaks at about 7.41, 8.57, 18.27 and 21.01 degrees in term of two theta. In some embodiments, form I has an XRPD comprising one or more peaks at about 7.41, 8.57, 12.13, 14.18, 15.02, 15.39, 15.98, 17.08, 18.27, 18.73, 21.01, 21.92, 22.31, 22.91, 24.66, 25.36, 28.27, 28.61 and 29.07 degrees in term of two theta. In some embodiments, form I has an XRPD substantially as depicted in FIG. 9 wherein the peak at about 21.01 degree in term of two theta has a relative intensity of at least about 50%, at least about 60%, at least about 70%, at least about 80%, at least about 90% or at least about 99% with respect to the strongest peak in the XRPD.

In certain embodiments, the characteristics of form I can be detected, identified, classified and characterized using well-known techniques such as, but not limited to, melting point. The melting point of form I is at about 185.8° C. to about 186.3° C.

In some embodiments, the crystalline form of azilsartan is crystalline form J. In some embodiments, form J of azilsartan disclosed herein is substantially pure. In some embodiments, form J has an XRPD comprising a peak at about 23.32 degree in term of two theta. In some embodiments, form J has an XRPD comprising one or more peaks at about 21.30, 22.81 and 23.32 degrees in term of two theta. In some embodiments, form J has an XRPD comprising one or more peaks at about 7.61, 19.00, 21.30, 22.10, 22.81, 23.32 and 25.05 degrees in term of two theta. In some embodiments, form J has an XRPD comprising one or more peaks at about 2.10, 4.93, 7.61, 8.64, 9.50, 10.99, 13.17, 13.64, 14.30, 15.12, 15.57, 16.25, 17.21, 18.49, 19.00, 19.99, 21.30, 22.10, 22.81, 23.32, 24.19, 25.05, 25.55, 25.96, 27.43, 28.64, 29.04 and 30.43 degrees in term of two theta. In some embodiments, form J has an XRPD substantially as depicted in FIG. 10 wherein the peaks at about 23.32 degree in term of two theta has a relative intensity of at least about 50%, at least about 60%, at least about 70%, at least about 80%, at least about 90% or at least about 99% with respect to the strongest peak in the XRPD.

In certain embodiments, the characteristics of form J can be detected, identified, classified and characterized using well-known techniques such as, but not limited to, melting point. The melting point of form J is at about 192.4° C. to about 195.7° C.

In some embodiments, the crystalline form of azilsartan is crystalline form K. In some embodiments, form K of azilsartan disclosed herein is substantially pure. In some embodiments, form K has an XRPD comprising a peak at about 21.16 degree in term of two theta. In some embodiments, form K has an XRPD comprising one or more peaks at about 7.58, 8.52, 17.03, 21.16, 21.56, 22.14 and 22.88 degrees in term of two theta. In some embodiments, form K has an XRPD comprising one or more peaks at about 7.58, 8.52, 13.77, 15.05, 15.56, 17.03, 18.67, 19.03, 19.27, 20.04, 21.16, 21.56, 22.14, 22.88, 23.31, 23.66, 25.08, 25.36, 27.48, 28.65 and 28.90 degrees in term of two theta. In some embodiments, form K has an XRPD substantially as depicted in FIG. 11 wherein the peak at about 21.16 degree in term of two theta has a relative intensity of at least about 50%, at least about 60%, at least about 70%, at least about 80%, at least about 90% or at least about 99% with respect to the strongest peak in the XRPD.

In certain embodiments, the characteristics of form K can be detected, identified, classified and characterized using well-known techniques such as, but not limited to, melting point. The melting point of form K is at about 194.4° C. to about 196.5° C.

According to the present invention, the X-ray powder diffraction of forms A-K of azilsartan was measured using CuK alpha radiation, wherein an ordinate or Y-axis is diffraction intensities in counts/second (cps) and an abscissa or X-axis is the diffraction angle two theta in degrees.

It is worth noting that, for the X-ray powder diffraction peaks of a particular crystalline form, the two theta values may change slightly from one machine to another, from one sample to another. The difference in value may be about 1 degree, about 0.8 degrees, about 0.5 degrees, about 0.3 degrees, or about 0.1 degrees. Therefore, the above-mentioned values of two theta cannot be regarded as absolute.

For the melting point of a particular crystalline form, the melting point may change slightly from one machine to another, and from one sample to another. The difference in value may be less than or equal to about 5° C., or less than or equal to about 4° C., or less than or equal to about 3° C., or less than or equal to about 2° C. Therefore, the melting points given above cannot be regarded as absolute.

Also disclosed herein is a method for preparing the crystalline forms A-K of azilsartan, wherein the process comprises changing any one of the forms of azilsartan disclosed herein to another form of azilartan. The crystalline forms of azilsartan obtained from the process disclosed herein can be form A, form B, form C, form D, form E, form F, form G, form H, form I, form J or form K and wherein the novel crystalline form of azilsartan is substantially pure.

Azilsartan can be prepared by using the disclosed processes in the Chinese patent application CN 93100006.8.

The process for preparing the crystalline form of azilsartan comprising: dissolving azilsartan in a good solvent to form a solution; and forming crystals by cooling the solution.

In some embodiments, the crystalline forms disclosed herein can be prepared by anti-solvent crystallization (aka precipitation crystallization, salting out or drowning out). Anti-solvent crystallization generally achieves supersaturation and solidification by exposing a solution of a product to one or more solvents in which the product is sparingly soluble. The anti-solvent crystallization can be carried out by a batch, semi-batch or continuous process or operation.

In certain embodiments, the anti-solvent crystallization is carried out by a batch or semi-batch process. The batch or semi-batch process generally includes adding either the anti-solvent to the product solution (normal addition) or the product solution to the anti-solvent (reverse addition).

When an anti-solvent is added to the product solution, supersaturation will develop. The amount of supersaturation created prior to nucleation generally is system specific and depends on the addition rate, mixing, primary or secondary nucleation rate, growth rate, feed location and the amount and type of impurities or seeds present in solution.

In some embodiments, a sufficient amount of a seed is added to promote a particular form of crystalline azilsartan such as any of forms A-K. A seed refers to a small single crystal from which a larger crystal of the same or different crystalline form is to be grown. In certain embodiments, the small single crystal and the larger crystal are of the same form. In some embodiments, the small single crystal and the larger crystal are of the different forms.

To achieve growth while minimizing the possibility for seed dissolution, the anti-solvent addition is stopped and seed is added at a point where the system is slightly supersaturated. An in-situ measuring devices based on a spectroscopy technique such as Fourier transform infrared or ultraviolet can be used to determine when the concentration reaches such a supersaturated point.

In some embodiments, the product solution is added to the anti-solvent resulting in a nucleation-controlled environment and formation of very fine particles.

In certain embodiments, seeding is used to avoid excessive nucleation. The seed can be added to the anti-solvent or product solution as a powder or in slurry form with the anti-solvent. In some embodiments, the seed can be conditioned via Ostwald ripening. In certain embodiments, the seed is added as a powder or in slurry at a point within the metastable zone of the system.

The addition of the anti-solvent to the product solution or the product solution to the anti-solvent may occur at a constant rate; or at an initial slow addition rate followed by a gradual increase in rate.

In certain embodiments, the anti-solvent crystallization is carried out by a continuous operation, which may promote small mean crystal size and narrow size distribution. In some embodiments, an in-line mixing device or a stirred vessel may be used in the continuous processing. Certain non-limiting examples of in-line mixing equipment include impinging jet mixers, vortex mixers, Y mixers, homogenizers and rotor-stator configurations. The anti-solvent and product solution (which may contain seeds) may be mixed with the in-line mixing equipment.

In certain embodiments, an impinging jet system is used wherein the system comprises an impinging jet mixer and a ripening tank for receiving and ripening the product following the contact of the product and anti-solvent streams in the impinging jet mixer. The ripening tank may comprise a stirrer. The ripening tank is designed to facilitate diffusion of the trapped mother liquor in the nucleated solids and can be batch or continuous. In some embodiments, seeds are added to the anti-solvent stream or the ripening vessel.

In some embodiments, the process further comprises the addition of one or more anti-solvents to the solution before or in cooling step to promote crystallization, wherein the solubility of azilsartan in the anti-solvent is lower than the good solvent. The solubility difference between the good solvent and anti-solvent is about 10%, 20%, 30%, 40%, 50%, 60%, 70% or 80%. The anti-solvent can be polar or non-polar solvent.

The good solvent or anti-solvent can be one or more polar solvents, one or more non-polar solvents or a combination thereof, wherein the good solvent or anti-solvent is selected from dimethyl formamide (DMF), dimethyl sulfoxide (DMSO), water, alcohol solvents, ether solvents, ketone solvents, ester solvents, aromatic hydrocarbon solvents, alkane solvents, nitrile solvents and combinations thereof, wherein the alcohol solvents are selected from methanol, ethanol, or 1,3-propanediol, 1,2-propylene glycol, 1,1,1-Trichloro-2-methylpropan-2-ol and combinations thereof, wherein the ether solvents are selected from tetrahydrofuran (THF), methyl tert-butyl ether (MTBE), 1,4-dioxane and combinations thereof, wherein the ketone solvents are selected from acetone, methyl ethyl ketone, or 4-methyl-2-pentanone and combinations thereof, wherein the ester solvents are selected from ethyl acetate, iso-propyl acetate, n-butyl acetate, tert-butyl acetate and combinations thereof, wherein the alkane solvents are selected from dichloromethane, chloroform, hexane, cyclohexane, pentane or heptane and combinations thereof, wherein the aromatic hydrocarbon solvents are selected from benzene, toluene and combinations thereof; wherein the nitrile solvents are selected from acetonitrile, malononitrile and combinations thereof.

According to the process of the present invention, methods to dissolve azilsartan in the good solvent comprises stirring, heating under reflux or a combination thereof.

In some embodiments, the temperature for crystallization can be from about −10° C. to about 40° C. In certain embodiments, the temperature can be from about −10° C. to about 25° C. In some embodiments, the temperature can be from about −10° C. to about 10° C. In certain embodiments, the temperature can be from about −10° C. to about 0° C. In some embodiments, the temperature can be from about 0° C. to about 10° C.

The crystals may be isolated and/or purified by vacuum filtration, gravity filtration, suction filtration and a combination thereof. The isolated crystal may carry mother liquor. Therefore, the isolated crystals may be further washed by suitable solvent and then dried. In certain embodiments, washing is done with the same solvent used in the process. In another embodiment, washing is done with an anti-solvent.

Also disclosed herein is a process for preparing crystalline form A of azilsartan which is substantially pure, wherein the good solvent or anti-solvent is selected from N,N-dimethylformamide (DMF), water, methanol, ethanol, THF, n-heptane, methylene chloride, DMSO, ethyl acetate, acetone, acetonitrile, 1,4-dioxo-dioxane, chlorobutanol, 4-methyl-2-pentanone, MTBE, 1,2-propanediol and combinations thereof.

In some embodiments, the good solvent or anti-solvent is selected from one or more of methanol, ethanol, acetone, ethyl acetate, acetonitrile, 1,4-dioxane, dichloromethane (DCM), MTBE, a mixed solvent of DMF and water, a mixed solvent of ethanol and water, a mixed solvent of 1,2-propylene glycol and water, a mixed solvent of DMSO and water, a mixed solvent of THF and water, a mixed solvent of methanol and ethanol, a mixed solvent of chlorobutanol and acetone, a mixed solvent of ethyl acetate and ethanol, a mixed solvent of methanol and n-heptane, a mixed solvent of DMSO and ethyl acetate, a mixed solvent of acetone and DMSO, a mixed solvent of THF and n-heptane, a mixed solvent of THF and DCM, a mixed solvent of acetone, DMF and water, a mixed solvent of DMF, DCM and water, a mixed solvent of 4-methyl-2-pentanone, ethanol and water, a mixed solvent of DMSO, n-heptane, ethyl acetate and water, a mixed solvent of DMSO, ethyl acetate, acetone and water.

Also provided herein is a process for preparing crystalline form B of azilsartan, wherein the good solvent is ether, more preferably THF, and wherein crystalline form B of azilsartan is substantially pure.

Also provided herein is a process for preparing crystalline form C of azilsartan, wherein the good solvent is THF, and wherein crystalline form C of azilsartan is substantially pure.

Also provided herein is a process for preparing crystalline form D of azilsartan, wherein the good solvent is DMF, and wherein crystalline form D is substantially pure.

Also provided herein is a process for preparing crystalline form E of azilsartan, wherein the good solvent is 1,4-dioxane, wherein the anti-solvent is water, and wherein crystalline form E of azilsartan is substantially pure.

Also provided herein is a process for preparing crystalline form F of azilsartan, wherein the good solvent is 4-methyl-2-pentanone or ethanol, wherein the anti-solvent is water, and wherein crystalline form F of azilsartan is substantially pure.

Also provided herein is a process for preparing crystalline form G of azilsartan, wherein the good solvent is THF, wherein the anti-solvent is water.

Also provided herein is a process for preparing crystalline form H of azilsartan, wherein the good solvent is methanol, wherein the anti-solvent is 1,4-dioxane or methyl tetrahydrofuran, and wherein crystalline form H of azilsartan is substantially pure.

Also provided herein is a process for preparing crystalline form I of azilsartan, wherein the good solvent is methyl tetrahydrofuran, isopropanol or methanol, wherein crystalline form I of azilsartan is substantially pure and wherein the anti-solvent is water.

Also provided herein is a process for preparing crystalline form J of azilsartan comprising dissolving azilsartan in good solvent such as THF, acetone or a combination thereof to form a solution, and then cooling the solution to obtain crystalline form J of azilsartan, wherein crystalline form J of azilsartan is substantially pure.

Also provided herein is a process for obtaining highly pure crystalline form K of azilsartan, the good solvent is selected from THF, acetone, chloroform, water, ethanol, toluene, 1,4-dioxane or a combination thereof. In some embodiments, the good solvent or anti-solvent is selected from a mixed solvent of 1,4-dioxane, acetone, and THF, a mixed solvent of chloroform and water, a mixed solvent of THF and ethanol, and a mixed solvent of toluene and THF.

The novel crystalline forms of azilsartan disclosed herein generally have good properties such as high solubility; thermal stability; better oral bioavailability; better dissolution profile for particular formulations; free-flowing; easily filterable; thermally stable which is suitable for particular formulations. The novel crystalline forms of azilsartan disclosed herein generally have good antistatic property which is convenient for operating the production process. The novel crystalline forms of azilsartan generally exhibit an excellent performance in reducing clinical systolic blood pressure (SBP) and average 24-hour SBP. Therefore novel crystalline forms of azilsartan can be used for preparing a pharmaceutical composition for the prevention or treatment of hypertension.

In illustrative embodiments of the present invention, novel crystalline form A, form B, form C, form D, form E, form F, form G, form H, form I, form J or form K of azilsartan is substantially pure, wherein the process for preparing the novel crystalline forms generally complies with the factory GMP production requirements, and is suitable for industrial production.

Also provided herein is a pharmaceutical composition comprising a therapeutically effective amount of a novel crystalline form disclosed herein such as form A, form B, form C, form D, form E, form F, form G, form H, form I, form J or form K of azilsartan and one or more pharmaceutically acceptable carriers, excipients or diluents.

In certain embodiments, the pharmaceutical composition comprises crystalline forms of azilsartan, wherein the pharmaceutical compositions that are compacted into a dosage form, such as tablets, pills, powders and granules. The pharmaceutical compositions may include excipients or carriers, wherein the excipients or carriers comprise sodium citrate, calcium phosphate, fillers, binders, moisturizers, disintegrants, retarders, absorption enhancer, wetting agents, absorbents, lubricants and a combination thereof, wherein the fillers include starch, lactose, sucrose, glucose, mannitol, silicic acid and a combination thereof, wherein the binders include carboxymethylcellulose, alginates, gelatin, polyvinylpyrrolidone, sucrose, gum Arabic and a combination thereof; wherein the moisturizers include glycerol, wherein the disintegrants include agar-agar, calcium carbonate, potato starch or tapioca starch, alginic acid, certain silicates, and sodium carbonate, low substituted hydroxypropyl cellulose and a combination thereof; wherein the blockers solution include paraffin; wherein the absorption enhancer include quaternary ammonium compounds; wherein the wetting agents include cetyl alcohol, monostearic acid glyceride and a combination thereof; wherein the absorbents include kaolin, bentonite and a combination thereof; wherein the lubricants include talc, calcium stearate, magnesium stearate, solid polyethylene glycols, sodium lauryl sulfate and a combination thereof.

The crystalline form of azilsartan disclosed herein or the pharmaceutical composition disclosed herein can be used in preventing or treating hypertension in a patient.

Also provided herein is a method of preventing or treating hypertension in a patient by administering to the patient a pharmaceutically effective amount of the crystalline form of azilsartan disclosed herein or the pharmaceutical composition disclosed herein.

Also provided herein is use of a pharmaceutical composition comprising a therapeutically effective amount of form A, form B, form C, form D, form E, form F, form G, form H, form I, form J or form K of azilsartan and one or more pharmaceutically acceptable carriers, excipients or diluents to treat conditions in a subject in need thereof; such as a strong and long lasting angiotensin II antagonistic activity and hypotensive action, and an insulin sensitizing activity, and circulatory diseases such as hypertension, cardiac diseases (e.g. cardiac hypertrophy, cardiac failure, cardiac infarction).

EXAMPLES

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. Furthermore, numeric ranges are provided so that the range of values is recited in addition to the individual values within the recited range being specifically recited in the absence of the range.

Example 1

Preparation of Crystalline Form A of Azilsartan

Azilsartan (2.0 g) was dissolved in DMF (5 mL) at 75° C. to form a solution. Water (10 mL) was added to the solution. The solution was stirred slowly while the temperature of the solution was lowered to about 25° C., kept at about 25° C. for 1 hour, cooled to about 10° C. and then kept at about 10° C. for 2 hours to form a precipitate. The precipitate was isolated by filtration and then dried under vacuum at about 55° C. for 12 hours. The precipitate was found to be crystalline form A of azilsartan having an XRPD as depicted in FIG. 1.

Example 2

Preparation of Crystalline Form A of Azilsartan

Azilsartan (2.0 g) was dissolved in methanol (20 mL) under reflux to form a solution. The solution was stirred slowly while the temperature of the solution was lower to about 25° C. The solution was kept at about 25° C. for 1 hour, cooled to about 10° C. and then kept at 10° C. for 2 hours to form a precipitate. The precipitate was isolated by filtration and then dried under vacuum at about 50° C. The precipitate was found to be crystalline form A of azilsartan having an XRPD as depicted in FIG. 1.

Example 3

Preparation of Crystalline Form A of Azilsartan

Azilsartan (2.0 g) was dissolved in ethanol (15 mL) under reflux to form a solution. The solution was stirred slowly while the temperature of the solution was lowered to about 25° C. The solution was kept at about 25° C. for 1 hour, cooled to about 10° C. and then kept at about 10° C. for 2 hours to form a precipitate. The precipitate was isolated by filtration and dried under vacuum at about 50° C. The precipitate was found to be crystalline form A of azilsartan having an XRPD as depicted in FIG. 1.

Example 4

Preparation of Crystalline Form A of Azilsartan

Azilsartan (2.0 g) was dissolved in DMF (2 mL) at room temperature to form a solution. Acetone (10 mL) was added to the solution and then the solution was heated to about 60° C., and then filtered. Water (20 mL) was added dropwise and the temperature of the solution was cooled to room temperature to form a precipitate. The precipitate was filtered and then dried under vacuum at about 50° C. The precipitate was found to be crystalline form A of azilsartan having an XRPD as depicted in FIG. 1.

Example 5

Preparation of Crystalline Form B of Azilsartan

Azilsartan (2.0 g) was dissolved in THF (10 mL) under reflux to form a solution. The solution was stirred slowly and the temperature of the solution was lowered to about 25° C. The solution was kept at about 25° C. for 1 hour, cooled to about 10° C. and then kept at about 10° C. for 2 hours to form a precipitate. The precipitate was filtered and then dried under vacuum at about 50° C. The precipitate was found to be crystalline form B of azilsartan having an XRPD as depicted in FIG. 2.

Example 6

Preparation of Crystalline Form C of Azilsartan

Azilsartan (4.0 g) was dissolved in THF (28 mL) under reflux to form a solution. The solution was stirred slowly and the temperature of the solution was lowered to about 32° C. The solution was kept at about 32° C. for 1 hour, cooled to about 10° C. and then kept at about 10° C. for about 30 minutes to form a precipitate. The precipitate was filtered and then dried under vacuum at about 50° C. to obtain a crude product.

The crude product (1 g) was dissolved in THF (7 mL) under reflux to form a solution. The solution was stirred slowly and the temperature of the solution was lowered to about 32° C. The solution was kept at about 32° C. for 1 hour, cooled to about 10° C. and then kept at about 10° C. for 30 minutes to form a precipitate. The precipitate was isolated by filtration. The precipitate was washed twice with dichloromethane (8 mL), and then dried under vacuum at about 50° C. The precipitate was found to be crystalline form C of azilsartan having an XRPD as depicted in FIG. 3.

Example 7

Preparation of Crystalline Form D of Azilsartan

Azilsartan (2 g) was dissolved in DMF (2.5 mL) at about 80° C. to form a solution. The solution was then stirred for about 30 minutes and the temperature of the solution was lowered to room temperature. The solution was kept at room temperature till a precipitate was formed. The precipitate was filtered, and then dried under vacuum at about 50° C. The precipitate was found to be crystalline form D of azilsartan having an XRPD as depicted in FIG. 4.

Example 8

Preparation of Crystalline Form E of Azilsartan

Azilsartan (2 g) was dissolved in 1,4-dioxane (15 mL) at about 100° C. to form a solution. The solution was stirred for about 30 minutes and the temperature of the solution was lowered to about 10° C. The solution was filtered and then water (100 mL) was added to the solution. The solution was stood until a precipitate was formed and then stirred overnight. The precipitate was filtered and then dried under vacuum at about 50° C. The precipitate was found to be crystalline form E of azilsartan having an XRPD as depicted in FIG. 5.

Example 9

Preparation of Crystalline Form F of Azilsartan

Azilsartan (3.5 g) was dissolved in a mixed solvent of 4-methyl-2-pentanone (20 mL) and ethanol (10 mL) at about 70° C. to form a solution. Water (60 mL) was added to the solution. A precipitate was formed. The solution was stirred for about 30 minutes and then stood overnight. The precipitate was then filtered and then dried under vacuum at about 50° C. The precipitate was found to be crystalline form F of azilsartan having an XRPD as depicted in FIG. 6.

Example 10

Preparation of Crystalline Form G of Azilsartan

Azilsartan (1.0 g) was dissolved in a mixed solvent of THF (7 mL) and water (7 mL) at about 67° C. to form a solution. The solution was cooled to about 32° C. and then uncovered for 48 hours to form a precipitate. The precipitate was filtered and then dried under vacuum at about 50° C. The precipitate was found to be crystalline form G of azilsartan having an XRPD as depicted in FIG. 7.

Example 11

Preparation of Crystalline Form H of Azilsartan

Azilsartan (1.0 g) was added to a mixed solvent of methanol (15 mL) and 1,4-dioxane (2 mL) and then heated under reflux at about 70° C. Azilsartan was dissolved to form a solution. The solution was then cooled to about 30° C. to form a precipitate. The precipitate was filtered and then dried under vacuum at about 55° C. overnight. The precipitate was found to be crystalline form H of azilsartan having an XRPD as depicted in FIG. 8.

Example 12

Preparation of Crystalline Form H of Azilsartan

Azilsartan (1.0 g) was added to methanol (15 mL), stirred and heated under reflux at 70° C. Azilsartan was not completely dissolved. 2-methyltetrahydrofuran (6 mL) was added slowly to the solution. Azilsartan gradually became fluffy. The solution was stirred for 1 hour and then cooled to room temperature to form a precipitate. The precipitate was filtered and then dried under vacuum at 55° C. overnight. The precipitate was found to be crystalline form H of azilsartan having an XRPD as depicted in FIG. 8.

Example 13

Preparation of Crystalline Form I of Azilsartan

Azilsartan (1.0 g) was added to methyltetrahydrofuran (8 mL) and stirred at about 70° C. Azilsartan gradually became fluffy. 2-methyltetrahydrofuran (12 mL) was added slowly to the solution. The solution was stirred while the temperature of the solution was lowered to room temperature to form a precipitate. The precipitate was isolated by filtration and then dried under vacuum at about 55° C. overnight. The precipitate was found to be crystalline form I of azilsartan having an XRPD as depicted in FIG. 9.

Example 14

Preparation of Crystalline Form I of Azilsartan

Azilsartan (1.5 g) was dissolved in a solvent of 1:1 methanol:water (10 mL) to form a solution. The solution was stirred at room temperature for 2 days to form a precipitate. The precipitate was filtered and then dried under vacuum at 55° C. The precipitate was found to be crystalline form I of azilsartan having an XRPD as depicted in FIG. 9.

Example 15

Preparation of Crystalline Form J of Azilsartan

Azilsartan (1.0 g) was dissolved in a mixed solvent of THF (11 mL) and acetone (18 mL) at about 68° C. with stirring to form a solution. The solution was cooled to about 5° C. and uncovered at room temperature overnight to form a precipitate. The precipitate was filtered and then dried under vacuum at about 55° C. overnight. The precipitate was found to be crystalline form J of azilsartan having an XRPD as depicted in FIG. 10.

Examples 16

Preparation of Crystalline Form K of Azilsartan

Azilsartan (1.0 g) was dissolved in a mixed solvent of THF (8 mL) and ethanol (20 mL) at about 70° C. with stirring to form a solution. The solution was cooled to about 5° C. No precipitate was formed. The solution was stood at room temperature overnight to form a precipitate. The precipitate was filtered and dried under vacuum at about 55° C. overnight. The precipitate was found to be crystalline form K of azilsartan having an XRPD as depicted in FIG. 11.

Example 17

Preparation of Crystalline Form K of Azilsartan

Azilsartan (1.0 g) was added to toluene (12 mL), stirred and heated under reflux at about 70° C. to form a solution. Azilsartan was not completely dissolved. THF (6 mL) was added slowly to the solution. Azilsartan gradually became fluffy. The solution was stirred for 1 hour while the temperature of the solution was lowered to room temperature to form a precipitate. The precipitate was filtered and then dried under vacuum at about 55° C. overnight. The precipitate was found to be crystalline form K of azilsartan having an XRPD as depicted in FIG. 11.

Example 18

Preparation of Crystalline Form K of Azilsartan

Azilsartan (0.3 g) was added to a mixed solvent of chloroform (150 mL) and water (40 mL) to form a solution. The solution was stirred for 2 hours at about 70° C., cooled to room temperature to form a precipitate. The precipitate was isolated by filtration. The precipitate was found to be crystalline form K of azilsartan having an XRPD as depicted in FIG. 11.

Example 19

Preparation of Crystalline Form K of Azilsartan

Azilsartan (1.0 g) was added to THF (8.5 mL), stirred and heated under reflux at about 68° C. to form a solution. After the solution became clear, a lot of white solid precipitate was formed suddenly. The solution was cooled to room temperature. The precipitate was filtered and then dried under vacuum at about 55° C. overnight. The precipitate was found to crystalline form K of azilsartan having an XRPD as depicted in FIG. 11.

Example 20

Preparation of Crystalline Form K of Azilsartan

Azilsartan (1.0 g) was added to 1,4-dioxane (8 mL), stirred and heated under reflux at about 70° C. to form a solution. 1,4-dioxane (7 mL) was further added to the solution with stirring. Azilsartan became gradually fluffy. The solution was cooled to room temperature to form a precipitate. The precipitate was filtered and then dried under vacuum at about 55° C. overnight. The precipitate was found to be crystalline form K of azilsartan having an XRPD as depicted in FIG. 11.

Example 21

The Solubility of Crystalline Forms A, B, C and D of Azilsartan

The solubility of crystalline forms A, B, C and D was measured in accordance with the solubility test described in "Chinese Pharmacopoeia 2010", Topic and Requirement 15. A crystalline form of azilsartan was grinded into powder. The powder (300 mg) was added to 6 ml of 0.1M HCl as the solvent at 25° C.±2° C. The solid was dissolved by shaking for 30 seconds every 5 minutes and then the solubility of the solid was observed with eyes. The total test time was 30 minutes. The solid was deemed as dissolved when no solid was detected in the mixture by human eyes. The solubility data of crystalline forms A, B, C and D of azilsartan are as shown below.

TABLE 1

The solubility data of crystalline forms A, B, C and D of azilsartan in 6 ml of 0.1M HCl

| Sample | solvent | The weight of sample (mg) | The volume of solvent (mL) | Result |
|---|---|---|---|---|
| Form A | 0.1M HCl | 300 | 6 | dissolved |
| Form B | 0.1M HCl | 300 | 6 | dissolved |
| Form C | 0.1M HCl | 300 | 6 | dissolved |
| Form D | 0.1M HCl | 300 | 6 | dissolved |

The data show that crystalline forms A, B, C and D of azilsartan are very soluble.

Example 22

The Stabilities of Crystalline Form A of Azilsartan

Thermal Stability

A layer of crystalline form A having a thickness of less than 5 mm was place in a flat weighing bottle. The layer was placed at 60° C. for 15 days. Samples were taken out at 6 days, 11 days and 16 days and examined for purity by HPLC, appearance and crystalline form.

Humidity Stability

A layer of crystalline form A having a thickness of less than 5 mm was place in a flat weighing bottle. The layer was placed at 25° C. and relative humidity (RH) of 90%+/−5% for 15 days. Samples were taken out at 5 days, 10 days and 15 days and examined for purity by HPLC, appearance and crystalline form.

Light Stability

A layer of crystalline form A having a thickness of less than 5 mm was place in a flat weighing bottle. The layer was illuminated by light having an illuminance of 4500+/−500 Lux for 15 days. Samples were taken out at 6 days, 11 days and 16 days and examined for purity by HPLC, appearance and crystalline form.

The conditions for the HPLC measurements are as shown below.

Instrument: Agilent 1200HPLC
Column: Agilent Eclipse XDB-C18 4.6*150 mm, 5 μm
Detection wavelength: 254 nm
Mobile phase: A phase 10 mM ammonium acetate (pH=3.5) and B phase acetonitrile

TABLE 2

Elution conditions:

| Time (min.) | A Phase | B Phase | Flow (mL/min.) |
|---|---|---|---|
| 0 | 65% | 35% | 0.8 |
| 15 | 65% | 35% | 0.8 |
| 30 | 25% | 75% | 0.8 |
| 45 | 25% | 25% | 0.8 |

Stop time: 45 minutes
Post Time: 8 minutes
Column temperature: 30° C.

The results of the thermal, humidity and light stabilities of crystalline form A of azilsartan are shown in Table 3.

TABLE 3

The results of the thermal, humidity and light stabilities of crystalline form A of azilsartan:

| | | RT* (min.) | | | | | | | |
|---|---|---|---|---|---|---|---|---|---|
| | | 2.39 | 2.89 | 3.9 | 5.79 | 20.55 | 22.8 | 23.6 | 26.96 | 27.5 |
| Thermal Stability | 0 day | — | 0.01% | 0.32% | — | — | 0.04% | 0.01% | — | 0.06% |
| | 6 days | — | 0.02% | 0.33% | 0.01% | 0.01% | 0.04% | 0.02% | 0.01% | 0.06% |
| | 11 days | — | 0.01% | 0.35% | — | 0.02% | 0.04% | 0.02% | — | 0.07% |
| | 16 days | — | 0.01% | 0.35% | — | 0.02% | 0.04% | 0.02% | — | 0.07% |
| Light stability | 6 days | 0.01% | 0.09% | 0.32% | — | — | 0.04% | 0.01% | — | 0.06% |
| | 11 days | 0.04% | 0.14% | 0.61% | 0.02 | 0.07% | 0.06% | 0.03% | 0.01% | 0.29% |
| | 16 days | 0.05% | 0.22% | 0.34% | — | — | 0.04% | 0.01% | — | 0.09% |
| Humidity stability | 6 days | — | 0.02% | 0.31% | 0.01 | — | 0.05% | 0.02% | — | 0.07% |
| | 11 days | — | 0.02% | 0.33% | — | — | 0.04% | 0.02% | — | 0.06% |
| | 16 days | — | 0.01% | 0.32% | — | — | 0.04% | 0.01% | — | 0.05% |

| | | RT* (min.) | | | Appearance | Crystalline form |
|---|---|---|---|---|---|---|
| | | 28.81 | 30.66 | 13.2 | | |
| Thermal Stability | 0 day | — | 0.02% | 99.51% | White or off-white powder | Form A |
| | 6 days | 0.01% | 0.03% | 99.47% | White or off-white powder | Form A |
| | 11 days | — | 0.02% | 99.48% | White or off-white powder | Form A |
| | 16 days | — | 0.02% | 99.47% | White or off-white powder | Form A |
| Light stability | 6 days | — | 0.02% | 99.45% | Light yellow powder | Form A |
| | 11 days | 0.01% | 0.03% | 98.71% | Light yellow powder | Form A |
| | 16 days | — | — | 99.24% | Light yellow powder | Form A |

TABLE 3-continued

The results of the thermal, humidity and light stabilities of crystalline form A of azilsartan:

| | | | | | | |
|---|---|---|---|---|---|---|
| Humidity stability | 6 days | — | 0.03% | 99.48% | White or off-white powder | Form A |
| | 11 days | — | 0.03% | 99.51% | White or off-white powder | Form A |
| | 16 days | — | 0.02% | 99.52% | White or off-white powder | Form A |

Note:
*RT refers to retention time. The RT of azilsartan is 13.2 minutes;
"—" refers to the peak area is less than 3000 or there is no peak.

What is claimed is:

1. A crystalline form of azilsartan, wherein the crystalline form is form A, form B, form C, form D, form E, form F, form G, form H, form I, form J or form K and wherein:
   a) form A has an X-ray powder diffraction pattern comprising peaks at 9.15, 18.34, 20.42, 21.49 and 23.53 degrees in term of two theta;
   b) form B has an X-ray powder diffraction pattern comprising peaks at 9.08, 21.41 and 23.47 degrees in term of two theta;
   c) form C has an X-ray powder diffraction pattern comprising peaks at 18.32, 21.85, 23.34 and 24.60 degrees in term of two theta;
   d) form D has an X-ray powder diffraction pattern comprising peaks at 9.33, 9.55, 20.83, 21.82, 25.05 and 26.23 degrees in term of two theta;
   e) form E has an X-ray powder diffraction pattern comprising peaks at 9.20, 10.42, 18.04, 21.53, 23.05, 23.57 and 23.89 degrees in term of two theta;
   f) form F has an X-ray powder diffraction pattern comprising peaks at 9.09, 9.22 and 18.29 degrees in term of two theta;
   g) form G has an X-ray powder diffraction pattern comprising peaks at 9.18 and 18.37 degrees in term of two theta;
   h) form H has an X-ray powder diffraction pattern comprising peaks at 7.52, 21.09, 22.05 and 23.21 degrees in term of two theta;
   i) form I has an X-ray powder diffraction pattern comprising peaks at 7.41, 8.57, 18.27 and 21.01 degrees in term of two theta;
   j) form J has an X-ray powder diffraction pattern comprising peaks at 21.30, 22.81 and 23.32 degrees in term of two theta; or
   k) form K has an X-ray powder diffraction pattern comprising peaks at 7.58, 8.52, 17.03, 21.16, 21.56, 22.14 and 22.88 degrees in term of two theta.

2. The crystalline form of azilsartan of claim 1, wherein the crystalline form is form A, wherein form A has an X-ray powder diffraction pattern comprising peaks at 9.15, 12.75, 18.34, 18.68, 19.36, 19.97, 20.42, 21.49, 21.82, 23.53, 23.98 and 25.26 degrees in term of two theta; or an X-ray powder diffraction pattern comprising peaks at 9.15, 12.75, 14.91, 15.38, 17.98, 18.34, 18.68, 19.36, 19.97, 20.42, 21.49, 21.82, 23.53, 23.98, 24.60, 25.26, 25.53, 26.68, 27.72, 28.77, 29.11 and 29.40 degrees in term of two theta; or an X-ray powder diffraction pattern substantially as depicted in FIG. 1 wherein the peak at 9.15 degree in term of two theta has a relative intensity of at least about 50%, at least about 60%, at least about 70%, at least about 80%, at least about 90% or at least about 99% with respect to the strongest peak in the X-ray powder diffraction pattern.

3. The crystalline form of azilsartan of claim 1, wherein the crystalline form is form B, wherein form B has an X-ray powder diffraction pattern comprising peaks at 7.63, 9.08, 18.62, 19.30, 21.41 and 23.47 degrees in term of two theta; or an X-ray powder diffraction pattern comprising peaks at 7.63, 9.08, 10.62, 12.69, 13.24, 15.34, 15.75, 16.53, 16.95, 18.27, 18.62, 19.08, 19.30, 19.64, 19.89, 20.10, 20.35, 21.41, 21.76, 22.21, 22.98, 23.47, 23.92, 24.31, 25.18, 25.48, 26.31 and 26.62 degrees in term of two theta; or an X-ray powder diffraction pattern substantially as depicted in FIG. 2 wherein the peak at 9.08 degree in term of two theta has a relative intensity of at least about 50%, at least about 60%, at least about 70%, at least about 80%, at least about 90% or at least about 99% with respect to the strongest peak in the X-ray powder diffraction pattern.

4. The crystalline form of azilsartan of claim 1, wherein the crystalline form is form C, wherein form C has an X-ray powder diffraction pattern comprising peaks at 9.13, 11.77, 15.74, 16.33, 18.32, 18.68, 21.85, 22.46, 23.34 and 24.60 degrees in term of two theta; or an X-ray powder diffraction pattern comprising peaks at 7.56, 9.13, 11.77, 13.97, 15.74, 16.33, 18.32, 18.68, 19.07, 19.72, 20.12, 20.77, 21.85, 22.12, 22.46, 22.83, 23.34, 24.12, 24.60, 25.20, 25.51, 26.91, 28.17, 29.87, 30.60 and 31.09 degrees in term of two theta; or an X-ray powder diffraction pattern substantially as depicted in FIG. 3 wherein the peak at 18.32 degree in term of two theta has a relative intensity of at least about 50%, at least about 60%, at least about 70%, at least about 80%, at least about 90% or at least about 99% with respect to the strongest peak in the X-ray powder diffraction pattern.

5. The crystalline form of azilsartan of claim 1, wherein the crystalline form is form D, wherein form D has an X-ray powder diffraction pattern comprising peaks at 9.33, 9.55, 11.65, 13.46, 14.99, 15.83, 17.69, 18.39, 19.11, 19.51, 20.16, 20.83, 21.36, 21.67, 21.82, 22.15, 22.38, 23.02, 23.48, 24.63, 25.05, 25.46, 25.99, 26.23, 27.09, 28.40, 29.09 and 32.49 degrees in term of two theta; or an X-ray powder diffraction pattern substantially as depicted in FIG. 4 wherein the peak at 9.33 degree in term of two theta has a relative intensity of at least about 50%, at least about 60%, at least about 70%, at least about 80%, at least about 90% or at least about 99% with respect to the strongest peak in the X-ray powder diffraction pattern.

6. The crystalline form of azilsartan of claim 1, wherein the crystalline form is form E, wherein form E has an X-ray powder diffraction pattern comprising peaks at 6.48, 9.20, 10.42, 11.36, 12.81, 14.97, 15.62, 16.32, 17.03, 18.04, 18.72, 19.00, 19.67, 20.55, 21.53, 23.05, 23.57, 23.89, 24.91, 25.65 and 26.70 degrees in term of two theta; or an X-ray powder diffraction pattern comprising peaks at 6.48, 6.87, 7.87, 9.20, 9.81, 10.42, 11.36, 11.94, 12.81, 14.97, 15.62, 16.32, 17.03, 18.04, 18.72, 19.00, 19.67, 20.55, 21.53, 23.05, 23.57, 23.89, 24.91, 25.65, 26.70, 27.61 and 28.80 degrees in term of two theta; or an X-ray powder diffraction pattern substantially as depicted in FIG. 5 wherein the peak at 23.89 degree in term of two theta has a relative intensity of at least about 50%, at least about 60%, at least about 70%, at least about 80%, at least about 90% or at least about 99% with respect to the strongest peak in the X-ray powder diffraction pattern.

7. The crystalline form of azilsartan of claim 1, wherein the crystalline form is form F, wherein form F has an X-ray powder diffraction pattern comprising peaks at 9.09, 9.22, 12.76, 18.29, 18.44, 18.71, 19.41, 20.01, 20.24, 20.44, 21.45, 21.82, 23.44, 23.54, 24.01, 25.30, 25.65, 26.72, 28.86, 29.10, 37.14 and 37.26 degrees in term of two theta; or an X-ray powder diffraction pattern substantially as depicted in FIG. 6 wherein the peak at 9.09 degree in term of two theta has a relative intensity of at least about 50%, at least about 60%, at least about 70%, at least about 80%, at least about 90% or at least about 99% with respect to the strongest peak in the X-ray powder diffraction pattern.

8. The crystalline form of azilsartan of claim 1, wherein the crystalline form is form G, wherein form G has an X-ray powder diffraction pattern comprising peaks at 7.51, 8.52, 9.18, 10.96, 12.74, 13.12, 13.56, 14.22, 15.03, 15.43, 16.22, 17.10, 17.96, 18.37, 18.71, 19.38, 19.97, 20.47, 21.16, 21.53, 21.85, 22.07, 22.71, 23.17, 23.54, 24.02, 24.96, 25.36, 25.78 and 26.72 degrees in term of two theta; or an X-ray powder diffraction pattern substantially as depicted in FIG. 7 wherein the peak at 9.18 degree in term of two theta has a relative intensity of at least about 50%, at least about 60%, at least about 70%, at least about 80%, at least about 90% or at least about 99% with respect to the strongest peak in the X-ray powder diffraction pattern.

9. The crystalline form of azilsartan of claim 1, wherein the crystalline form is form H, wherein form H has an X-ray powder diffraction pattern comprising peaks at 7.52, 8.45, 14.93, 18.92, 19.94, 21.09, 22.05, 22.71, 23.21, 24.98 and 28.80 degrees in term of two theta; or an X-ray powder diffraction pattern comprising peaks at 7.52, 8.45, 9.44, 10.97, 12.45, 13.14, 13.61, 14.15, 14.93, 15.40, 16.18, 16.95, 18.32, 18.92, 19.94, 21.09, 22.05, 22.71, 23.21, 23.52, 24.98, 25.26, 25.71, 27.22, 28.47, 28.80, 29.22 and 30.15 degrees in term of two theta; or an X-ray powder diffraction pattern substantially as depicted in FIG. 8 wherein the peak at 21.09 degree in term of two theta has a relative intensity of at least about 50%, at least about 60%, at least about 70%, at least about 80%, at least about 90% or at least about 99% with respect to the strongest peak in the X-ray powder diffraction pattern.

10. The crystalline form of azilsartan of claim 1, wherein the crystalline form is form I, wherein form I has an X-ray powder diffraction pattern comprising peaks at 7.41, 8.57, 12.13, 14.18, 15.02, 15.39, 15.98, 17.08, 18.27, 18.73, 21.01, 21.92, 22.31, 22.91, 24.66, 25.36, 28.27, 28.61 and 29.07 degrees in term of two theta; or an X-ray powder diffraction pattern substantially as depicted in FIG. 9 wherein the peak at 21.01 degree in term of two theta has a relative intensity of at least about 50%, at least about 60%, at least about 70%, at least about 80%, at least about 90% or at least about 99% with respect to the strongest peak in the X-ray powder diffraction pattern.

11. The crystalline form of azilsartan of claim 1, wherein the crystalline form is form J, wherein form J has an X-ray powder diffraction pattern comprising peaks at 7.61, 19.00, 21.30, 22.10, 22.81, 23.32 and 25.05 degrees in term of two theta; or an X-ray powder diffraction pattern comprising peaks at 2.10, 4.93, 7.61, 8.64, 9.50, 10.99, 13.17, 13.64, 14.30, 15.12, 15.57, 16.25, 17.21, 18.49, 19.00, 19.99, 21.30, 22.10, 22.81, 23.32, 24.19, 25.05, 25.55, 25.96, 27.43, 28.64, 29.04 and 30.43 degrees in term of two theta; or an X-ray powder diffraction pattern substantially as depicted in FIG. 10 wherein the peak at 23.32 degree in term of two theta has a relative intensity of at least about 50%, at least about 60%, at least about 70%, at least about 80%, at least about 90% or at least about 99% with respect to the strongest peak in the X-ray powder diffraction pattern.

12. The crystalline form of azilsartan of claim 1, wherein the crystalline form is form K, wherein form K has an X-ray powder diffraction pattern comprising peaks at 7.58, 8.52, 13.77, 15.05, 15.56, 17.03, 18.67, 19.03, 19.27, 20.04, 21.16, 21.56, 22.14, 22.88, 23.31, 23.66, 25.08, 25.36, 27.48, 28.65 and 28.90 degrees in term of two theta; or an X-ray powder diffraction pattern substantially as depicted in FIG. 11 wherein the peak at 21.16 degree in term of two theta has a relative intensity of at least about 50%, at least about 60%, at least about 70%, at least about 80%, at least about 90% or at least about 99% with respect to the strongest peak in the X-ray powder diffraction pattern.

13. A process for preparing the crystalline form of azilsartan of claim 1, comprising dissolving azilsartan in a good solvent to form a solution; and forming crystals by cooling the solution.

14. The process of claim 13 further comprising adding an anti-solvent to the solution before cooling.

15. The process of claim 13 or 14, wherein the good solvent or the anti-solvent is one or more polar solvents, one or more non-polar solvents or a combination thereof, and wherein the good solvent or the anti-solvent is selected from dimethyl formamide, dimethyl sulfoxide, water, alcohol solvents, ether solvents, ketone solvents, ester solvents, aromatic hydrocarbon solvents, alkane solvents, nitrile solvents and combinations thereof.

16. The process of claim 15, wherein the alcohol solvents are selected from methanol, ethanol, 1,3-propanediol, 1,2-propylene glycol, 1,1,1-Trichloro-2-methylpropan-2-ol and combinations thereof, wherein the ether solvents are selected from tetrahydrofuran, methyl tert-butyl ether, 1,4-dioxane and combinations thereof, wherein the ketone solvents are selected from acetone, methyl ethyl ketone, 4-methyl-2-pentanone and combinations thereof, wherein the ester solvents are selected from ethyl acetate, iso-propyl acetate, n-butyl acetate, tert-butyl acetate and combinations thereof, wherein the alkane solvents are selected from dichloromethane, chloroform, hexane, cyclohexane, pentane, heptane and combinations thereof, wherein the aromatic hydrocarbon solvents are selected from benzene, toluene and combinations thereof; wherein the nitrile solvents are selected from acetonitrile, malononitrile and combinations thereof.

17. A pharmaceutical composition comprising the crystalline form of azilsartan of claim 1 and one or more of inert excipients or carriers.

18. A method of treating hypertension in a patient by administering to the patient a pharmaceutically effective amount of the crystalline form of azilsartan of claim 1 or the pharmaceutical composition of claim 17.

19. The crystalline form of azilsartan of claim 1, wherein the crystalline form of azilsartan is substantially pure.

* * * * *